United States Patent
Weaver et al.

(10) Patent No.: US 9,750,885 B2
(45) Date of Patent: Sep. 5, 2017

(54) PLUNGER-DRIVEN AUTO-INJECTORS

(71) Applicant: Unitract Syringe Pty Ltd, Sydney (AU)

(72) Inventors: Philip A. Weaver, Denver, PA (US); Katlin M. Lumme, Mableton, GA (US)

(73) Assignee: UNL Holdings LLC, New York, NY (US)

( * ) Notice: Subject to any disclaimer, the term of this patent is extended or adjusted under 35 U.S.C. 154(b) by 294 days.

(21) Appl. No.: 14/258,569

(22) Filed: Apr. 22, 2014

(65) Prior Publication Data
US 2014/0330216 A1    Nov. 6, 2014

Related U.S. Application Data

(60) Provisional application No. 61/817,981, filed on May 1, 2013.

(51) Int. Cl.
*A61M 5/31*    (2006.01)
*A61M 5/315*    (2006.01)
(Continued)

(52) U.S. Cl.
CPC ...... *A61M 5/31513* (2013.01); *A61M 5/2033* (2013.01); *A61M 5/3232* (2013.01);
(Continued)

(58) Field of Classification Search
CPC .......... A61M 2005/206; A61M 5/2033; A61M 5/3234; A61M 5/326; A61M 5/24; A61M 5/3232; A61M 5/502
See application file for complete search history.

(56) References Cited

U.S. PATENT DOCUMENTS 3,395,704 A    8/1968    Frey et al.
5,425,715 A    6/1995    Dalling et al.
(Continued)

FOREIGN PATENT DOCUMENTS

AU    2003275893 B2    6/2004
CN    100553700 C    10/2009
(Continued)

OTHER PUBLICATIONS

European Patent Office, Written Opinion in International Patent Application No. PCT/US2014/034974, 7 pages (Jul. 28, 2014).

*Primary Examiner* — Scott Medway
(74) *Attorney, Agent, or Firm* — Hamilton, Brook, Smith & Reynolds, P.C.

(57) ABSTRACT

Plunger sub-assemblies for automatic injectors include a plunger outer having one or more engagement prongs, a plunger inner having one or more engagement slots which correspond with the engagement prongs of the plunger outer, and a retraction biasing member. The retraction biasing member is retained in a first energized state between the plunger outer and plunger inner when the engagement prongs of the plunger outer are releasably engaged with the engagement slots of the plunger inner. The one or more engagement prongs are capable of flexing substantially radially to release from engagement with the engagement slots of the plunger inner to permit the retraction biasing member to expand from the first energized state to a second expanded state. An automatic injector having a plunger sub-assembly includes a housing, an activation mechanism, and a plunger sub-assembly at least partially mounted within a syringe cartridge having a needle assembly.

17 Claims, 15 Drawing Sheets

(51) Int. Cl.
*A61M 5/32* (2006.01)
*A61M 5/20* (2006.01)

(52) U.S. Cl.
CPC ......... *A61M 5/3234* (2013.01); *A61M 5/3157* (2013.01); *A61M 2005/206* (2013.01); *A61M 2005/2073* (2013.01); *A61M 2207/00* (2013.01); *Y10T 29/49904* (2015.01)

(56) References Cited

U.S. PATENT DOCUMENTS

| | | | |
|---|---|---|---|
| 6,083,199 | A | 7/2000 | Thorley et al. |
| 6,090,070 | A | 7/2000 | Hager et al. |
| 6,387,078 | B1 | 5/2002 | Gillespie, III |
| 6,607,508 | B2 | 8/2003 | Knauer |
| 7,381,201 | B2 | 6/2008 | Gilbert et al. |
| 7,500,967 | B2 | 3/2009 | Thorley et al. |
| 7,736,353 | B2 | 6/2010 | Reynolds |
| 7,744,582 | B2 | 6/2010 | Sadowski et al. |
| 7,935,087 | B2 | 5/2011 | Judd et al. |
| 8,002,745 | B2 | 8/2011 | Kaal et al. |
| 8,021,333 | B2 | 9/2011 | Kaal et al. |
| 8,052,654 | B2 | 11/2011 | Kaal et al. |
| 8,114,050 | B2 | 2/2012 | Kaal et al. |
| 8,167,937 | B2 | 5/2012 | Cerruti et al. |
| 8,366,669 | B2 | 2/2013 | Donald et al. |
| 8,702,653 | B2 | 4/2014 | Samandi et al. |
| 8,808,244 | B2 | 8/2014 | Adlon et al. |
| 2001/0037087 | A1 | 11/2001 | Knauer |
| 2005/0080377 | A1 | 4/2005 | Sadowski et al. |
| 2005/0277886 | A1 | 12/2005 | Hommann et al. |
| 2006/0184137 | A1 | 8/2006 | Reynolds |
| 2009/0254048 | A1 | 10/2009 | Hetherington |
| 2011/0015572 | A1 | 1/2011 | Thorley et al. |
| 2011/0092954 | A1 | 4/2011 | Jennings |
| 2012/0056019 | A1 | 3/2012 | Renz et al. |
| 2013/0060232 | A1* | 3/2013 | Adlon et al. .................. 604/506 |

FOREIGN PATENT DOCUMENTS

| | | |
|---|---|---|
| CN | 101730558 A | 6/2010 |
| DE | 20 2009 003009 U1 | 6/2009 |
| EP | 2331171 | 6/2011 |
| FR | 1538565 A | 9/1968 |
| JP | 2007-504867 A | 3/2007 |
| JP | 2008-543500 A | 12/2008 |
| WO | WO 94/21316 A1 | 9/1994 |
| WO | WO 95/04562 A1 | 2/1995 |
| WO | WO 03/008023 A1 | 1/2003 |
| WO | WO 2004/000395 A1 | 12/2003 |
| WO | WO 2004/047890 A1 | 6/2004 |
| WO | WO 2004/047891 A1 | 6/2004 |
| WO | WO 2005/018721 A1 | 3/2005 |
| WO | WO 2006/108243 A2 | 10/2006 |
| WO | WO 2006/119570 A1 | 11/2006 |
| WO | WO 2007/002052 A2 | 1/2007 |
| WO | WO 2007/036676 A1 | 4/2007 |
| WO | WO 2009/003234 A1 | 1/2009 |
| WO | WO 2009/007229 A1 | 1/2009 |
| WO | WO 2009/063030 A1 | 5/2009 |
| WO | WO 2009/153540 A1 | 12/2009 |
| WO | WO 2009/153543 A1 | 12/2009 |
| WO | WO 2010/049239 A1 | 5/2010 |
| WO | WO 2011/057335 A1 | 5/2011 |
| WO | WO 2011/075760 A1 | 6/2011 |
| WO | WO 2013/028906 A1 | 6/2011 |
| WO | WO 2011/089417 A1 | 7/2011 |
| WO | WO 2011/109205 A1 | 9/2011 |
| WO | WO 2011/137488 A1 | 11/2011 |
| WO | WO 2011/141907 A1 | 11/2011 |
| WO | WO 2012/098371 A1 | 7/2012 |

\* cited by examiner

US 9,750,885 B2

PLUNGER-DRIVEN AUTO-INJECTORS

CROSS-REFERENCE TO RELATED APPLICATIONS

This application claims priority to U.S. Provisional Application No. 61/817,981, filed on May 1, 2013, which is included by reference herein in its entirety for all purposes.

FIELD

THIS INVENTION relates to automatic injectors for retractable syringes. More particularly, this invention relates to plunger sub-assemblies for automatic injectors and automatic injectors for retractable syringes having low retraction activation force, the methods of operating such devices, and the methods of assembling such devices.

BACKGROUND

Manually activated syringes are commercially available from a variety of manufacturers, including the owner and assignee of the present invention, and are used in the administration of drug solutions, drug suspensions, vaccines, medicinal therapies, and any other liquid medicament by parenteral injection. Such syringes are commonly utilized by medical practitioners to administer injections to patients but are difficult to use by self-administering patients.

An auto-injector is an automatic injection device designed to facilitate delivery of a dose of medicament to a patient through a hypodermic needle, the injection usually being administered by the patient themselves. An auto-injector works, for example, by delivering an injection automatically upon activation by the patient. This is in contrast to a conventional manually activated syringe where the patient themselves needs to directly depress a plunger into a barrel containing medicament in order to effect the injection. Auto-injectors have proven particularly useful in allowing the medically untrained user to administer a parenteral injection, and can provide both psychological and physical advantages to patients. Patients needing to inject medication for chronic disease management have used auto-injectors since the first reusable auto injector was introduced in the 1990s. An auto injector provides protection for the primary container, generally a pre-filled syringe, and offers an easy-to-use solution for automatic injection of medication. As used herein, the terms "automatic injector" and "auto-injector" are meant to refer to the same devices.

In addition to automatic needle insertion and dose delivery, some auto-injectors also incorporate safety mechanisms to automatically protect the patient from the needle after use. The automatic injectors of the prior art are usually provided with needle shields which extend over the needle when actuated. However, such safety mechanisms may fail to actuate and/or can be easily reversed, thereby leaving the patient exposed to the needle and susceptible to injury. Additionally, known automatic injectors generally link visual, tactile or audible indicators to the end of plunger stroke or actuation of some safety mechanism, instead of to the end of drug dose. Accordingly, the self-administering patient is not provided with an indication that the drug has been fully delivered and may remove the needle or actuate the safety mechanisms prematurely.

SUMMARY

The present invention provides plunger sub-assemblies for automatic injectors and automatic injectors for retractable syringes having low retraction activation force, the methods of operating such devices, and the methods of assembling such devices. The automatic injectors of the present invention provide integrated safety features which automatically retract the needle or cannula into the device to, for example, prevent injuries related to accidental needlestick. Additionally, the embodiments of the present invention provide true end of dose indication to users, informing the user that the drug delivery has completed and that the device is safe for removal and disposal. Furthermore, the embodiments of the present invention provide plunger sub-assemblies which reduce forces required to activate refraction of the needle or cannula, thereby providing significant manufacturing, assembly, and operational benefits. As such, the present invention provides plunger-driven automatic injectors for use for the efficient and safe delivery of drugs or therapeutics to patients. Accordingly, the novel devices of the present invention alleviate one or more of the problems associated with prior art devices, such as those referred to above.

In one broad form, the present invention provides a plunger sub-assembly for an automatic injector, the plunger sub-assembly comprising a plunger inner and plunger outer that maintain a retraction biasing member in an initially energized state.

In an aspect of this broad form, the plunger sub-assembly comprises a plunger outer having one or more engagement prongs, a plunger inner having one or more engagement slots and a retraction biasing member, whereby the one or more engagement prongs and the one or more engagement slots are capable of releasable engagement to retain the retraction biasing member in an initially energized state between the plunger outer and the plunger inner.

In at least one embodiment, the plunger outer has two engagement prongs for releasable engagement with the engagement slot(s) of the plunger inner. The retraction biasing member, which may be a spring such as a compression spring, is retained in a first energized state between the plunger outer and plunger inner when the engagement prongs of the plunger outer are releasably engaged with the engagement slots of the plunger inner. In at least one embodiment, the retraction biasing member is a compression spring. The retraction spring may be held in the first energized state between a ledge of the plunger inner and a base of the plunger outer. The one or more engagement prongs are capable of flexing substantially radially to release from engagement with the engagement slots of the plunger inner to permit the retraction spring to expand from the first energized state to a second expanded state. In at least one embodiment, the plunger inner has a seal-engaging member to engage a complementary engagement recess of a plunger seal. The seal-engaging member may be, for example, a screw-threaded aspect that is capable of screwing into the engagement recess of the plunger seal.

In another broad form, the present invention provides an automatic injector having a plunger sub-assembly, wherein the automatic injector comprises a housing, an activation mechanism, and a plunger sub-assembly at least partially mounted within a syringe cartridge having a needle assembly.

In at least one aspect of this broad form, the automatic injector comprises a housing, a syringe cartridge, a needle assembly comprising a retractable needle and the plunger assembly of the aforementioned aspect at least partially mounted within the syringe cartridge, and an activation mechanism operable to facilitate sequential depression of the plunger assembly to deliver fluid contents of the syringe cartridge and subsequent retraction of the plunger inner when engaged with the retractable needle.

The automatic injector may further comprise an injection biasing member residing in an initial energized state substantially within the plunger inner. As previously described, in at least one embodiment, the plunger sub-assembly includes a plunger outer having one or more engagement prongs, a plunger inner having one or more engagement slots which correspond with or engage the engagement prongs of the plunger outer, and a refraction biasing member retained in a first energized state between said plunger outer and plunger inner when the engagement prongs of the plunger outer are releasably engaged with the engagement slots of the plunger inner. The injection biasing member suitably resides within the plunger inner and is held in an initial energized state between a locking plateau of the housing and a platform of the plunger inner. The injection biasing member and the retraction biasing member may be respective compression springs in at least one embodiment of the present invention.

The plunger sub-assembly preferably has one or more locking hooks at a proximal end of the plunger inner which initially engage a locking plateau. In a particular embodiment, the one or more locking hooks may initially directly engage the locking plateau at an interior proximal end of the housing. In at least one embodiment, the activation mechanism is capable of directly engaging or contacting the one or more locking hooks of the plunger sub-assembly to disengage the locking hooks from the locking plateau of the housing. The housing may further include one or more recesses on the inner surface of the housing wherein, when the one or more engagement prongs interface with the recesses, the substantially radial flexion of the engagement prongs into the recesses permits the engagement prongs to disengage from the engagement slots of the plunger inner. This disengagement permits the retraction biasing member to be released from the first energized state to a second expanded state for retraction of the needle assembly. In the specific context of a compression spring, this comprises expansion of the compression spring. Accordingly, little or no additional force is needed to disengage the plunger outer from the plunger inner beyond the force utilized to axially translate the plunger sub-assembly to the portion of the housing where the engagement prongs may radially flex into the recesses.

Accordingly, by user action on the activation mechanism, the activation mechanism engages or contacts the one or more locking hooks of the plunger sub-assembly to disengage the locking hooks from the locking plateau of the housing. This action permits the actuation spring to expand, thereby translating the plunger sub-assembly within the housing in the distal direction substantially along the axis of the automatic injector. As the engagement prongs of the plunger sub-assembly reach recesses within the inner surface of the housing, the one or more engagement prongs of the plunger outer are permitted to flex substantially radially to disengage from the corresponding engagement slots of the plunger inner. This action permits the retraction spring to expand, thereby translating the plunger inner in the proximal direction substantially along the axis of the automatic injector for refraction of the needle assembly. If the syringe cartridge contains a drug treatment, such as in the case of a pre-filled syringe, the function of the plunger sub-assembly may be utilized to insert a needle and deliver the drug treatment into a patient. Optionally, when a retractable syringe is utilized as a syringe cartridge, the actuation mechanism may further be utilized to activate a retraction mechanism.

In a preferred embodiment of the present invention, the syringe cartridge of the automatic injector is a retractable syringe. Such syringes may further contain safety features which retract the needle after use, providing desirable needle-stick prevention, and prevent re-use of the syringe. Suitably, the plunger sub-assembly is slidably moveable within the barrel of the syringe to thereby facilitate delivery of the drug treatment to a user, patient or other recipient. The retractable syringe may include a retractable needle assembly. Preferably, the plunger sub-assembly is capable of engaging or contacting the needle assembly, or a portion thereof, to cause retraction of the cannula or needle. Suitably, retraction of the needle is facilitated by a biasing member such as a spring, elastic or other member capable of storing and releasing energy to facilitate needle retraction. It will be appreciated that the retractable syringe may comprise any needle retraction mechanism that is operable with the automatic injector disclosed herein. By way of example, the needle retraction mechanism may be as described in one or more of the following, although without limitation thereto: U.S. Pat. Nos. 6,083,199, 7,500,967, 7,935,087, 8,021,333, 8,002,745, 8,052,654, 8,114,050, 8,167,937, and 8,361,035; U.S. Patent Pub. No. 2013/0226084; and International PCT App. Nos. PCT/AU2010/001677, PCT/US2012/067793, and PCT/US2014/024781 all of which are incorporated herein by reference, in their entirety, for all purposes.

According to one embodiment, the retractable syringe comprises: a needle assembly comprising the retractable needle, wherein the retractable needle comprises a cannula and a needle body. The needle assembly may further comprise a needle seal engageable by the plunger seal mounted to the plunger inner. Preferably, the needle assembly is configured such that the needle seal retains the retractable needle and the cannula of the retractable needle passes through the needle seal to permit delivery of one or more substances and/or mixed substances to a user, patient, or other recipient. In one embodiment, the needle assembly is similar to that disclosed in International PCT App. No. PCT/AU2010/001677 which includes a needle body that is capable of being captured by the plunger seal, such as within a recess within the plunger seal, for retraction into the barrel of the syringe cartridge and/or the housing of the automatic injector. In an alternative embodiment, the needle assembly may be similar to that disclosed in International PCT App. Nos. PCT/US2012/067793 or PCT/US2014/024781, which do not require a needle body and which activate retraction of the cannula generally through contact between the plunger seal and needle seal.

In at least one embodiment of the present invention, the automatic injector further includes a sleeve having one or more protrusions that are initially held by a cap in an engaged position within corresponding notches on the interior surface of housing. Upon removal of the cap, protrusions are permitted to flex radially inwards to disengage from the notches. The sleeve is configured to permit axial translation in a distal direction until a bridge portion of sleeve contacts a corresponding depth limiter on the interior surface of the housing. The automatic injector further includes one or more windows within the housing to view the internal components and function of the automatic injector. The windows may be transparent, opaque, or translucent, for example. The automatic injector may also include a tactile biasing member, such as a compression spring, between the activation mechanism and the proximal end of the housing.

In yet another broad form, the present invention provides a method of assembling an automatic injector. Suitably, the automatic injector is according to the aforementioned aspect.

In an aspect of this broad form, the method includes the steps of:

(i) inserting an injection biasing member into a housing and compressing the injection biasing member between the housing and the plunger inner, substantially or at least partially within a chamber of the plunger inner, by releasably engaging the plunger inner with the housing;

(ii) assembling a plunger sub-assembly by engaging one or more engagement prongs of a plunger outer one or more engagement slots of a plunger inner so that a retraction biasing member is retained in an initially energized state between said plunger outer and plunger inner; and (iii) inserting the plunger sub-assembly into the housing such that at least a portion of the plunger inner resides within a barrel of a syringe cartridge is permitted to axially translate therein.

In a preferred form, the method of assembly includes: (i) inserting an injection biasing member into a housing and compressing the injection biasing member between the housing and the plunger inner, substantially or at least partially within a chamber of the plunger inner, by detachably engaging one or more locking hooks of the plunger inner with a locking plateau of the housing; (ii) assembling a plunger sub-assembly including a plunger outer having one or more engagement prongs, a plunger inner having a corresponding engagement slots, and a retraction biasing member retained in a first energized state between said plunger outer and plunger inner when the engagement prongs of the plunger outer are releasably engaged with the engagement slots of the plunger inner; and (iii) inserting the plunger sub-assembly into the housing such that at least a portion of the plunger inner resides within a barrel of a syringe cartridge is permitted to axially translate therein. The injection biasing member is initially maintained in an energized state substantially within an upper portion of the plunger inner. In another embodiment, the method further includes the step of: attaching an activation mechanism to the housing wherein the activation mechanism is configured to contact the one or more locking hooks of the first actuation pill upon activation. The engagement prongs of the plunger outer are maintained in a releasably engaged configuration with the engagement slots of the plunger inner by a first inner diameter of the housing. The method may further include the steps of: (iv) filling a drug chamber of a syringe cartridge with a drug fluid, and (v) inserting the distal end of the plunger sub-assembly into the proximal end of the syringe cartridge. Steps (iv) and (v) may occur before or after step (iii).

Throughout this specification, unless otherwise indicated, "comprise," "comprises," and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to the following drawings wherein.

DETAILED DESCRIPTION

Figure 1A:
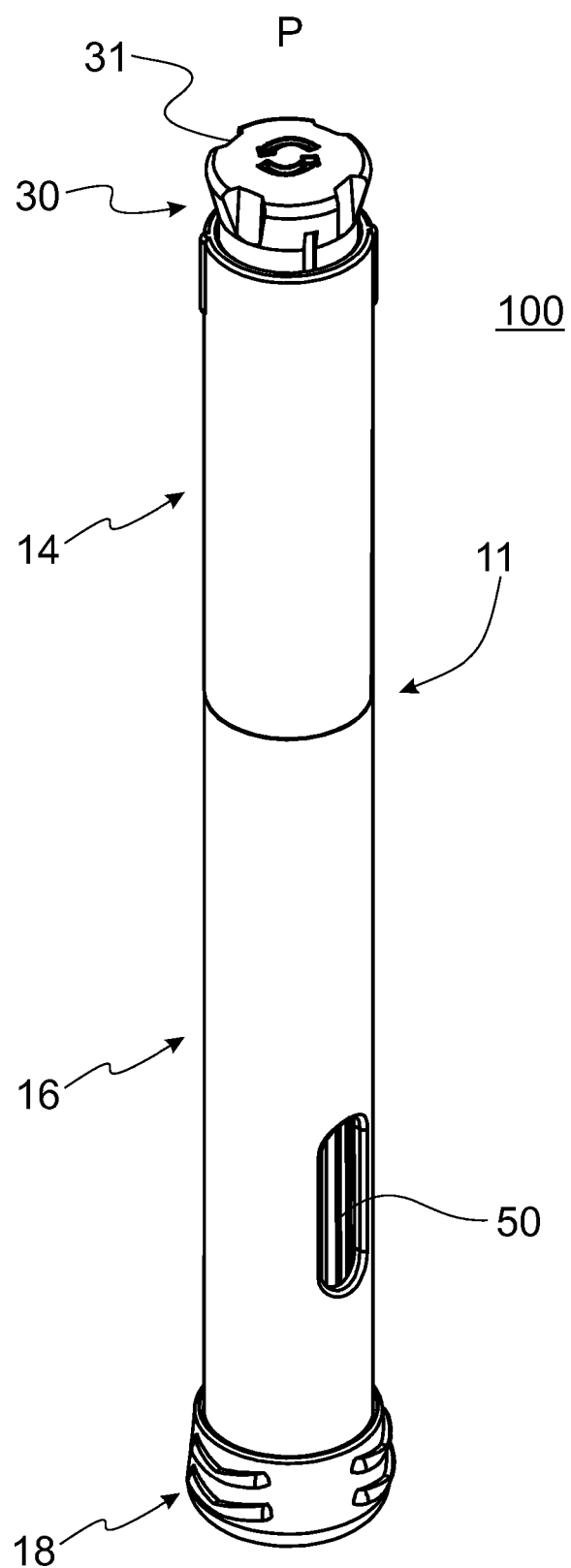
FIG. 1A shows an isometric view of an automatic injector, according to one embodiment of the present invention.

The novel devices of the present invention provide integrated safety features which automatically retract a needle or cannula into the device and provide true end of dose indication to users. Additionally, the embodiments of the present invention reduce the forces necessary to activate the needle retraction features of the device, thereby providing operational and manufacturing advantages. Such devices are safe and easy to use, and are aesthetically and ergonomically appealing for self-administering patients. The devices described herein incorporate features which make activation, operation, and lock-out of the device simple for even untrained users. The embodiments of the present invention provide these desirable features without any of the problems associated with known prior art devices.

As used herein to describe the actuation mechanisms, plunger sub-assemblies, automatic injectors, syringe cartridges, or any of the relative positions of the components of the present invention, the terms "axial" or "axially" refer generally to a longitudinal axis "A" around which the components of the automatic injectors are preferably positioned, although not necessarily symmetrically there-around. The term "radial" refers generally to a direction normal to axis A. The terms "proximal," "rear," "rearward,"

"back," or "backward" refer generally to an axial direction in the direction "P" of the activation mechanism. The terms "distal," "front," "frontward," "depressed," or "forward" refer generally to an axial direction in the direction "D" of the needle. As used herein, the term "glass" should be understood to include other similarly non-reactive materials suitable for use in a pharmaceutical grade application that would normally require glass. The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" does not include either glass or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration. "Fluid" refers primarily to liquids, but can also include suspensions of solids dispersed in liquids, and gasses dissolved in or otherwise present together within liquids inside the fluid-containing portions of syringes. The term "spring" is used herein with reference to one or more "biasing members," and any type of spring or other biasing member may be utilized within the inventions herein.

Figure 1B:
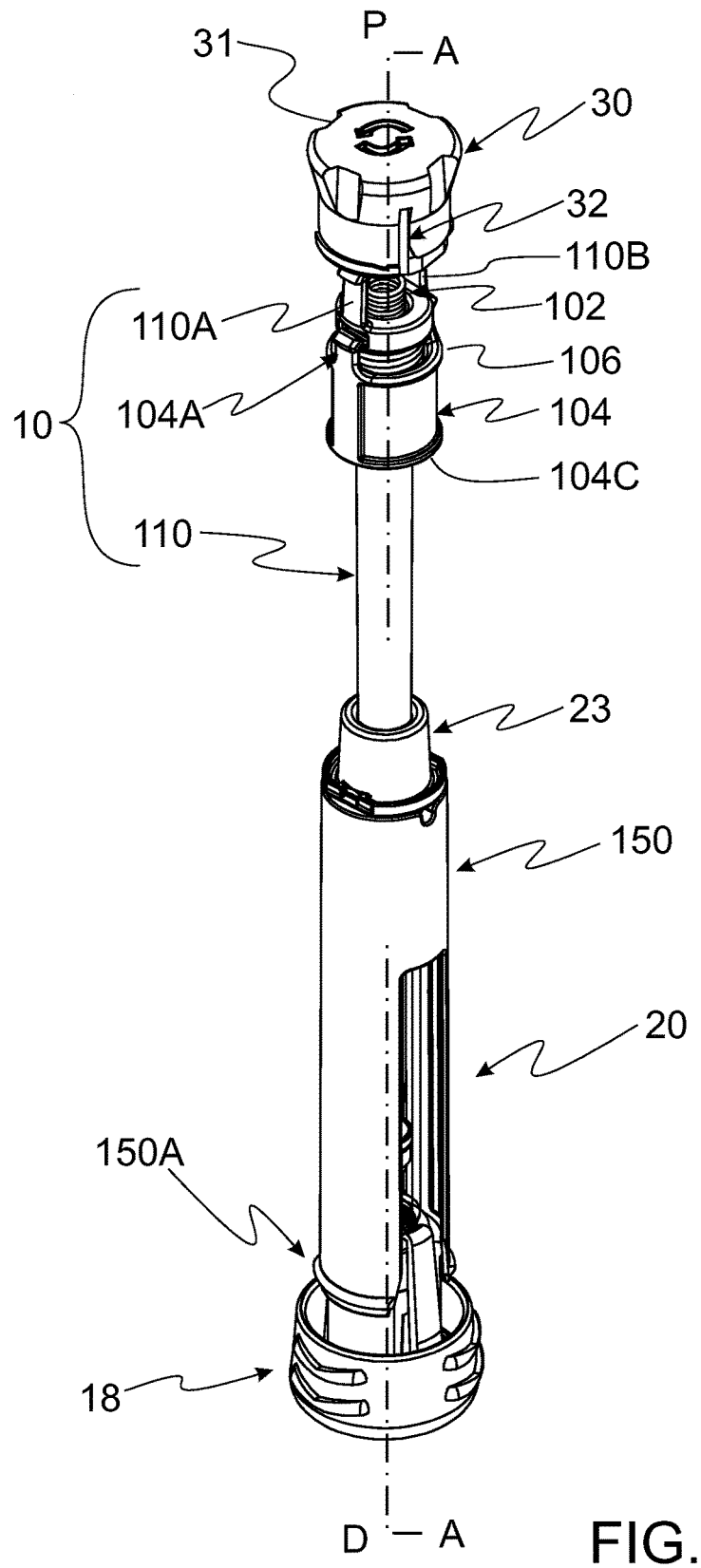
FIG. 1B shows an isometric view of the interior components of the automatic injector shown in FIG. 1A.
Figure 2:
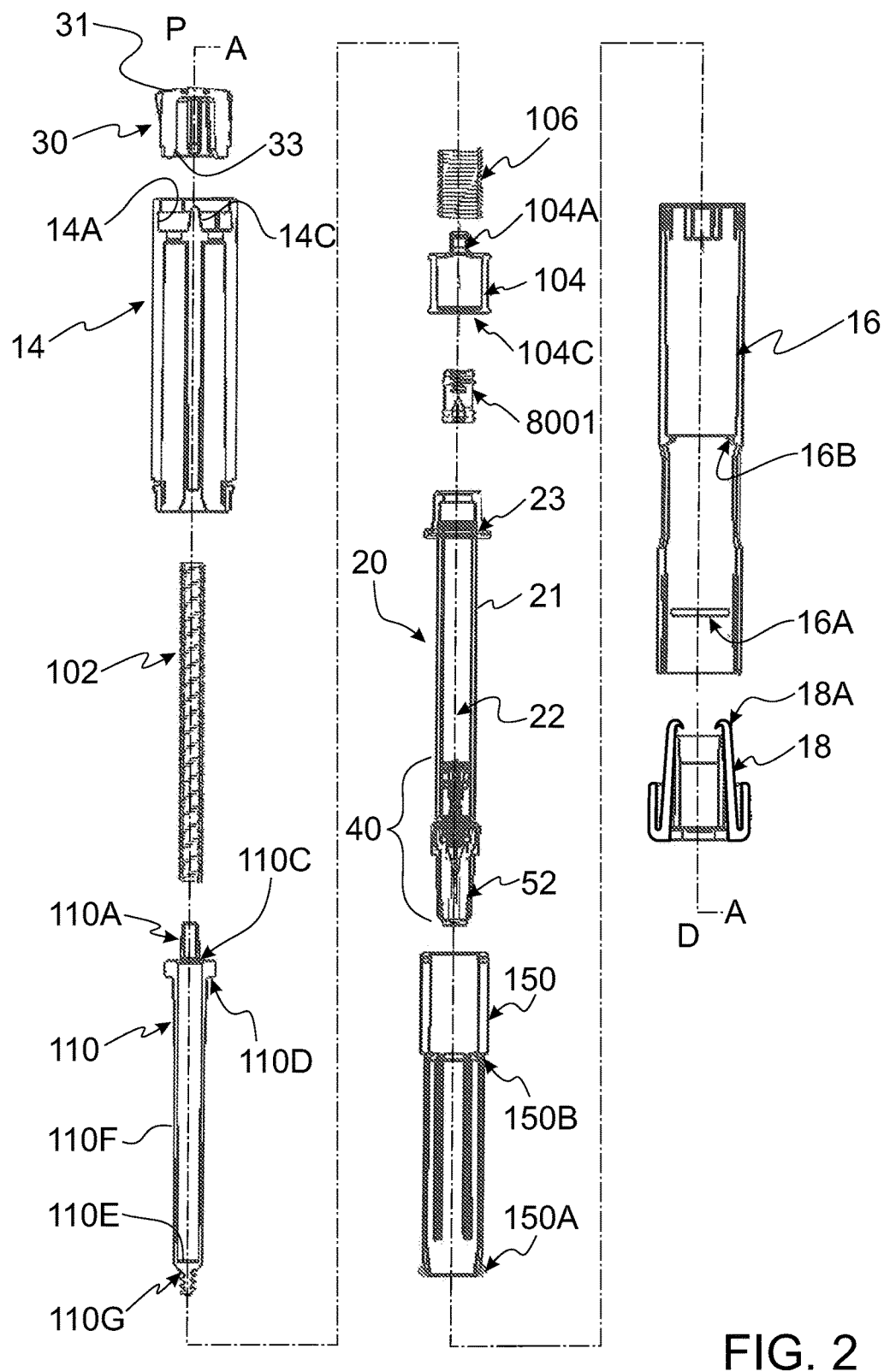
FIG. 2 shows an exploded view of an automatic injector, according to one embodiment of the present invention.

FIG. 1A and FIG. 1B show an embodiment of an automatic injector 100 having a plunger sub-assembly 10. The automatic injector 100 includes housing 11 that comprises upper housing 14 and lower housing 16. Upper housing 14 and lower housing 16 may be made of any of a number of materials including plastics, metals, and glass, but are preferably made of plastic. Housing 11 may be one unified or integrally formed component, may be formed from two or more portions or, as shown in FIGS. 1A and 1B, comprise upper and lower housings 14, 16. When upper housing 14 and lower housing 16 are two separate components they may be fixedly connected, for example by a glue or adhesive, or removably attached, for example by a screw-fit connection. Automatic injector 100 may also include activation mechanism 30 and cap 18. FIG. 1B shows the interior components of automatic injector 100, i.e., with the upper housing 14 and lower housing 16 hidden from view. As shown in FIG. 1B, automatic injector 100 includes activation mechanism 30, plunger sub-assembly 10, and syringe cartridge 20. The syringe cartridge 20 includes a barrel 21 and a needle assembly 40 mounted thereto, both of which are shown in FIG. 2. FIG. 2 shows how the plunger sub-assembly 10 and other components are assembled to produce an automatic injector 100, according to at least one embodiment of the present invention. The automatic injector may also include a sleeve 150 to assist in the positioning of the syringe cartridge 20 and needle assembly 40 throughout operation, as is described further herein with reference to FIGS. 5-8. Cap 18 may be removably attached to automatic injector 100 at the distal end D and removed at time of use by the user. FIG. 1B shows the components of plunger sub-assembly 10, the syringe cartridge 20 having needle assembly 40, and automatic injector 100 (with upper housing 14 removed to show the internal components), according to at least one embodiment of the present invention, in a locked configuration.

In at least one embodiment, the activation mechanism 30 comprises button 31 which may, for example, be rotated to unlock the activation mechanism 30 and then depressed to trigger the activation mechanism 30, as is detailed further herein. The activation mechanism 30 is shown at proximal end P. A tactile biasing member may be utilized, for example, to maintain the activation mechanism 30 in a locked position until manipulation by the user and/or to provide the user with a tactile feedback when the button 31 is depressed. The tactile biasing member may be, for example, a spring, or may comprise interacting surfaces of the upper housing 14 and the activation mechanism 30, as shown in FIGS. 5-8.

Typically, syringe cartridge 20 includes a barrel 21 having a drug chamber 22. A liquid substance or drug dose is held in the drug chamber 22 for delivery through a needle to a patient. Upon depression, i.e., axial motion in the distal direction, activation mechanism 30 permits plunger sub-assembly 10 to actuate the needle insertion and drug dose delivery stages of operation. The plunger sub-assembly 10 also translates plunger inner 110 in the distal direction to subsequently facilitate or initiate the retraction activation stage of operation. Retraction activation by the plunger sub-assembly 10 enables retraction of the needle into the barrel of the syringe cartridge 20 and automatic injector 100, as is detailed further herein.

The automatic injectors 100 of the present invention utilize one or more biasing members, such as compression springs 102, 106, to provide the force necessary to insert the needle into the user, push fluid from the drug chamber 22 of the syringe cartridge 20 out through the needle for drug delivery, and activate a needle retraction safety mechanism. However, it is important to minimize the force necessary to be provided by such biasing members for various manufacturing and operational benefits. For example, a lower force biasing member, which may be more cost-effective than higher force biasing members, may be utilized if reduced forces are needed to perform all of the stages of device operation. Similarly, reducing necessary forces may enable the devices to be stored and transported more readily since the energy stored within the device prior to activation is reduced. Accordingly, the embodiments of the present invention utilize plunger sub-assemblies 10 which require lower forces to initiate activation of the retraction mechanism. Because the plunger inner 110 and the integrated retraction features are driven, or caused to activate, by the plunger sub-assemblies 10, the plunger sub-assemblies 10 and the automatic injectors 100 of the present invention may be configured to utilize lower force biasing members, such as compression springs 102, 106. Similarly, because the total force necessary to: insert the needle into the user, deliver the drug fluid, and activate the needle retraction mechanism is reduced; a simplified plunger sub-assembly 10 may be utilized to efficiently deliver all of the force necessary for the operation of the device. This advantage of the plunger sub-assemblies 10 of the present invention provides substantial benefits to the manufacturability, stability, and operability of the automatic injectors 100 described herein.

FIG. 2 shows an exploded view of an automatic injector 100 comprising plunger sub-assembly 10 according to at least one embodiment of the present invention. As shown, an injection spring 102 may reside within a plunger inner 110, while a refraction spring 106 may reside between the plunger inner 110 and a plunger outer 104. This simplified plunger sub-assembly 10 permits the reduction of force necessary for the activation of the automatic injector 100.

Figure 3A:
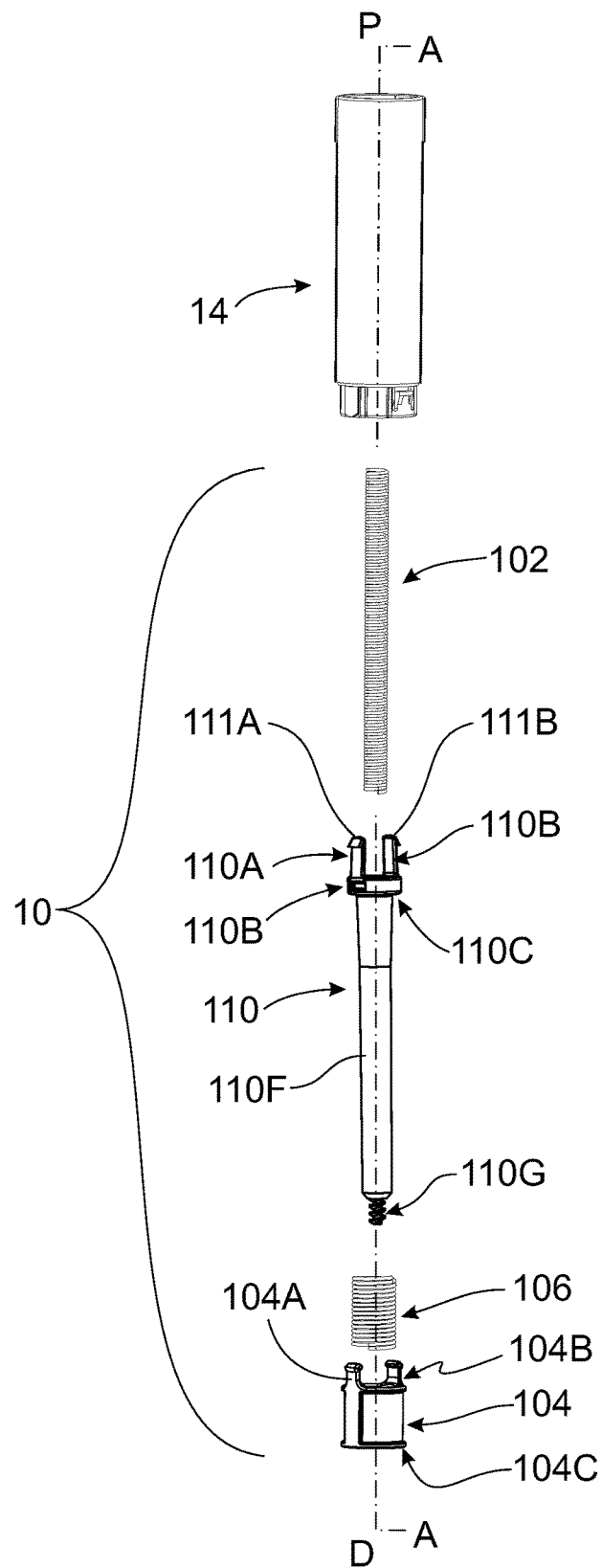
FIG. 3A shows an exploded view of a plunger sub-assembly for an automatic injector, according to one embodiment of the present invention.
Figure 3B:
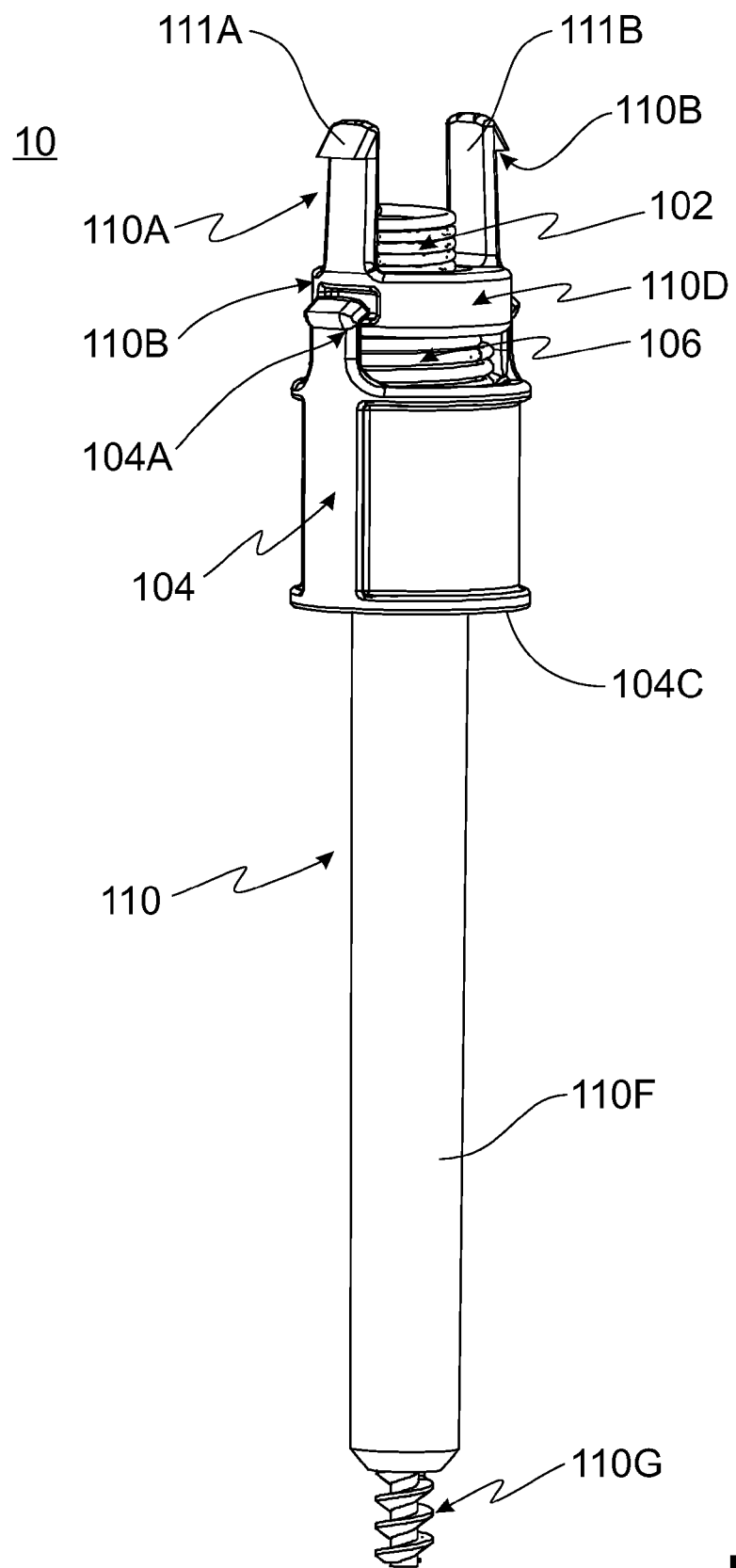
FIG. 3B shows an enlarged view of the plunger sub-assembly shown in FIG. 3A in an energized state.
Figure 3C:
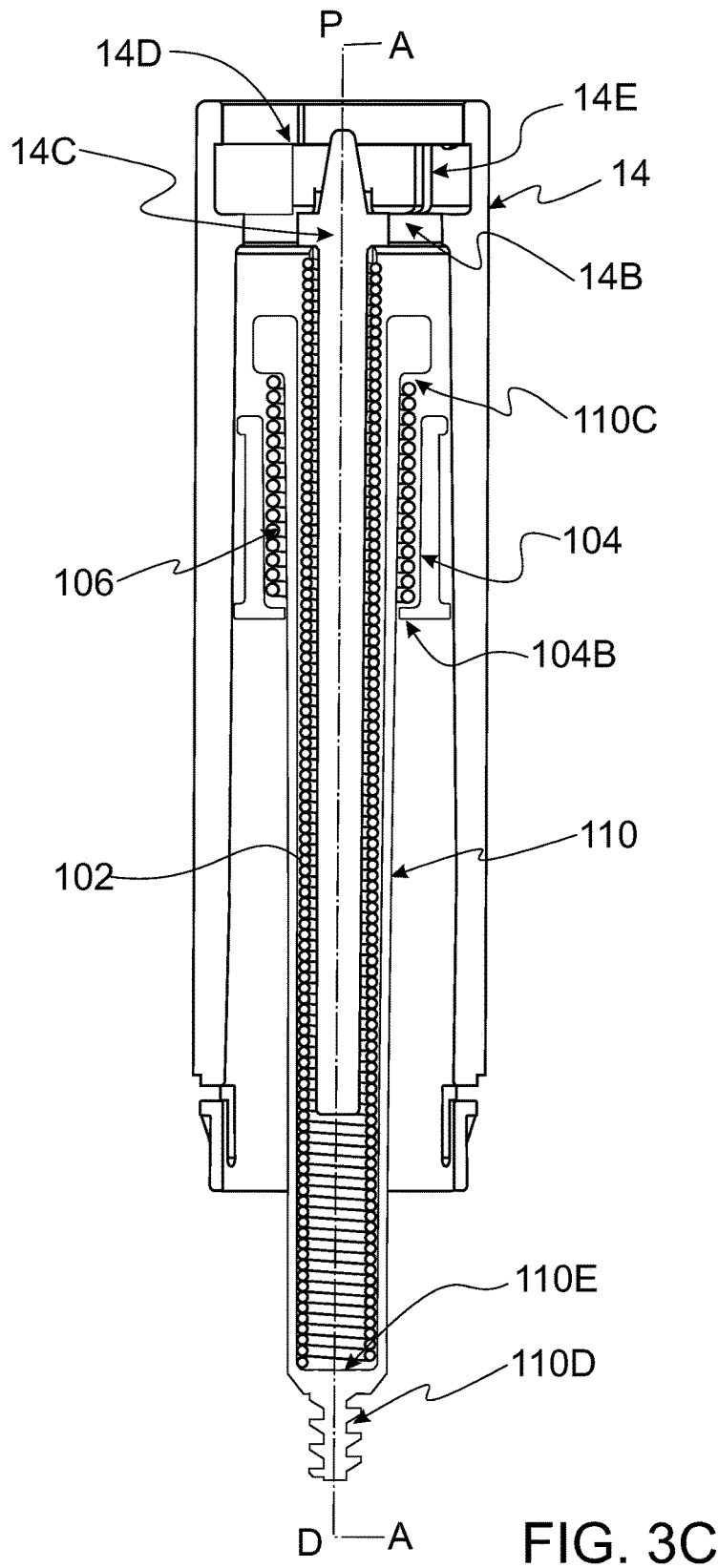
FIG. 3C shows a cross-sectional view of the plunger sub-assembly shown in FIG. 3A.
Figure 3D:
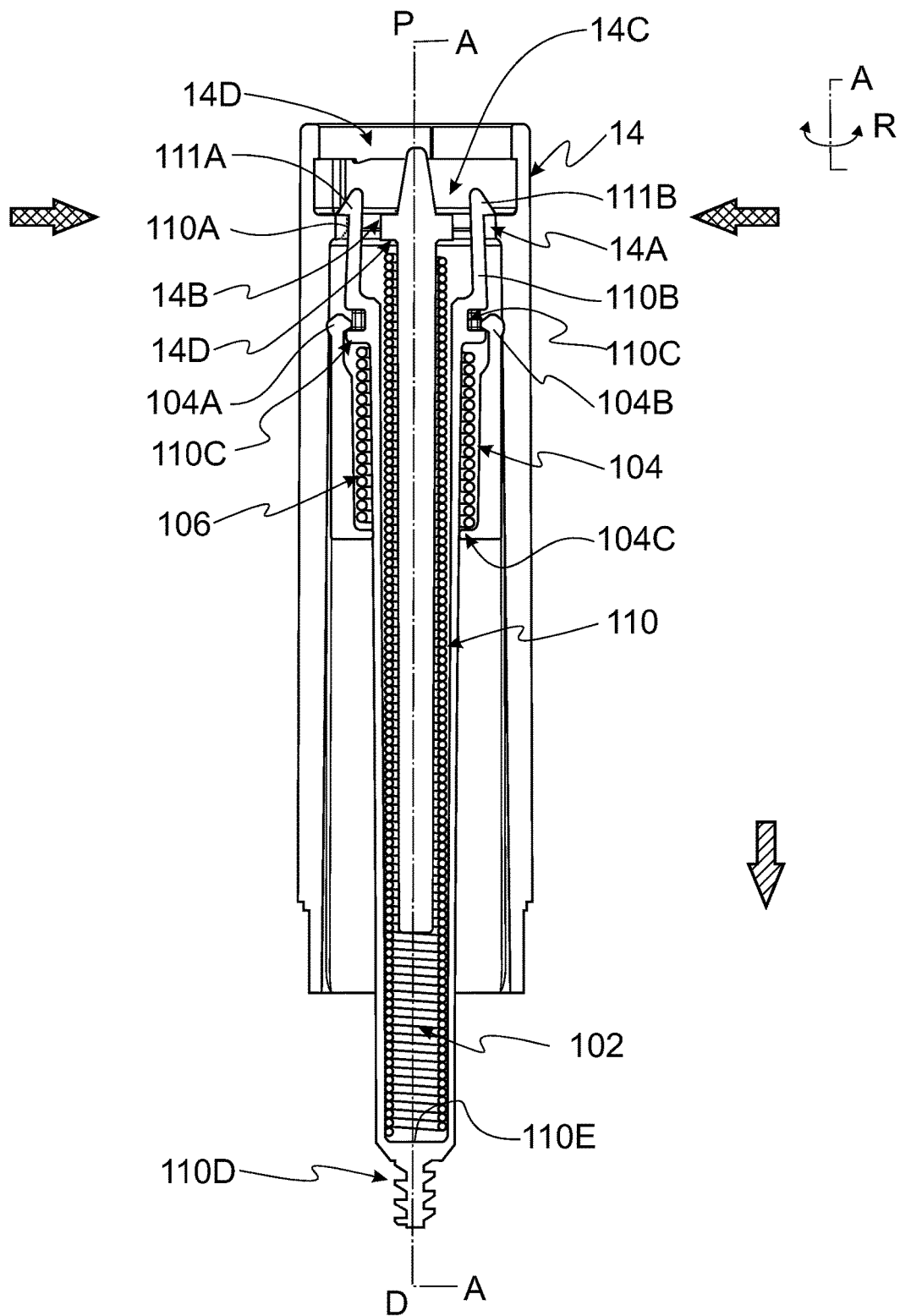
FIG. 3D shows a 90 degree rotation of the cross-sectional view shown in FIG. 3C.

FIGS. 3A-3D further detail the plunger sub-assembly 10, according to at least one embodiment of the present invention, which is a component of the automatic injector 100. FIG. 3A shows the components of plunger sub-assembly 10 in an exploded view, in addition to upper housing 14. FIG. 3B shows these components, without the upper housing 14, in an energized state prior to actuation. In at least one embodiment, plunger sub-assembly 10 includes injection spring 102 and plunger inner 110, and retraction spring 106 and plunger outer 104. In an energized configuration prior to actuation, the injection spring 102 rests in an energized state substantially within the plunger inner 110. The injection spring 102 is held in an energized state between, and upon activation caused to act on, a platform 110E of the plunger inner 110. In this energized configuration, plunger inner 110 is detachably connected to upper housing 14 within the interior 14C of the upper portion 14D of the upper housing 14, as shown in FIGS. 3C and 3D. Locking hooks 111A,B of respective locking members 110A,B of plunger inner 110 may initially directly engage locking plateau 14A of the upper housing 14, which may be caused to disengage therefrom by function of the activation mechanism (not shown) located at an upper portion 14D of the upper housing 14. For example, the activation mechanism, or aspects thereof, may cause flexion of the locking hooks 111A,B to disengage the locking hooks 111A,B from the locking plateau 14A of the upper housing 14. Upon disengagement of the locking hooks 111A,B from the locking plateau 14A, the injection spring 102 is permitted to expand from its energized state to axially translate the plunger sub-assembly 10 in the distal direction, as will be further explained herein.

FIGS. 3C-3D provide cross-sectional views of the plunger sub-assembly 10 at least partially within upper housing 14 prior to activation or actuation of the automatic injector 100. FIG. 3D shows a 90 degree axial rotation view of the view shown in FIG. 3C. As shown, locking hooks 111A,B of plunger inner 110 initially engage locking plateau 14A of upper housing 14. Upon activation of the automatic injector 100 by the activation mechanism 30, locking hooks 111A,B are caused to disengage from locking plateau 14A at housing pass-throughs 14B. In at least one embodiment, the locking hooks 111A,B are moved radially inwards (i.e., in the direction of the solid arrows shown in FIG. 3D) by corresponding interface surfaces of the activation mechanism 30 upon depression by the user, thereby causing disengagement of the plunger sub-assembly from the locking plateau 14A. As would be appreciated by an ordinarily skilled artisan, the term "hooks" is an example of any type of engagement mechanism including, for example, prongs, latches, tabs, and the like. Upon such disengagement, injection spring 102 is permitted to expand from its energized state, thereby exerting force upon platform 110E of the plunger inner 110 and axially translating plunger inner 110 (and plunger sub-assembly 10) in the distal direction. Because plunger inner 110 is slidably or detachably engaged with plunger outer 104, such as by the interaction between one or more engagement prongs 104A,B at the proximal end of a plunger outer 104 component of the plunger sub-assembly 10 and the engagement slot 110C of the plunger inner 110, axial translation of the plunger inner 110 in the distal direction causes the plunger outer 104 (and therefore the entire plunger sub-assembly 10) to similarly axially translate in the distal direction (i.e., in the direction of the hatched arrow shown in FIG. 3D). Accordingly, the force asserted by the injection spring 102 and the plunger inner 110 of the plunger sub-assembly 10, upon activation by the user, is utilized in the embodiments of the present invention to insert the needle into the user, to axially translate the plunger sub-assembly 10 in the distal direction to enable drug delivery, and to permit or facilitate activation of the retraction mechanism.

Figure 5:
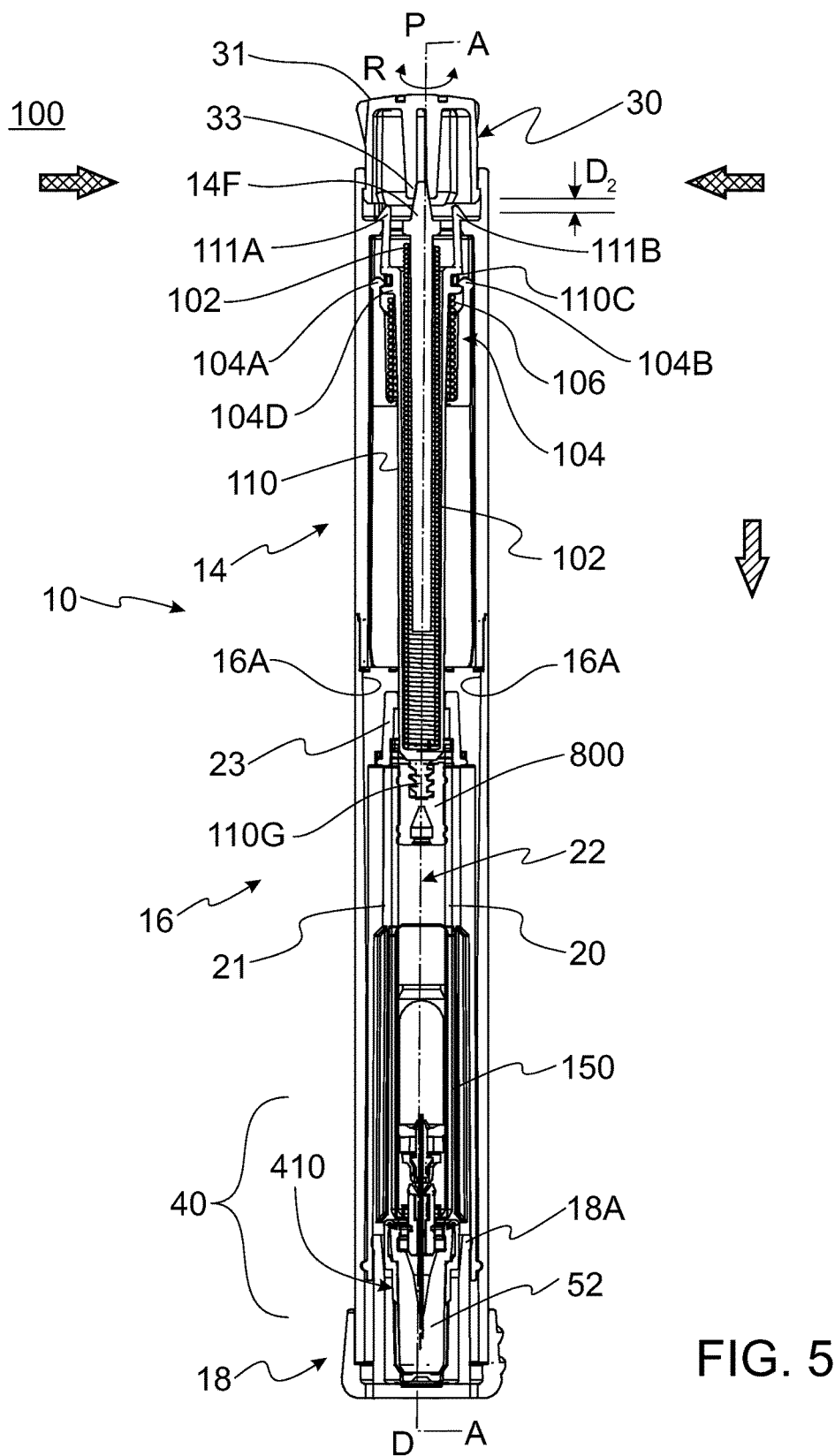
FIG. 5 shows an automatic injector including a plunger sub-assembly, according to one embodiment of the present invention, in a locked configuration.

Such operation of the plunger sub-assembly 10 is also shown in FIGS. 5-8, in which the plunger sub-assembly 10 is incorporated into an automatic injector 100. As shown in FIGS. 1B, 2, and 5, release ring 23 rests upon the proximal end of sleeve 150 to retain the syringe barrel 202 and needle assembly 40 of the syringe cartridge in an initial locked position within the automatic injector 100. In at least one embodiment, sleeve 150 has one or more protrusion 150A (visible in FIGS. 1B and 2) that are initially held in position within corresponding notches 16A (visible in FIG. 2) on the interior surface of lower housing 16. The notches 16A may be one or more separate notches, a notched ring around the interior circumference, or a number of other possible configurations which permit the one or more protrusions 150A to removably engage the notches 16A. In an initially locked configuration, locking extension 18A (visible in FIG. 2) of the cap 18 rest against the interior surface of the sleeve 150 and assert a radially outward force to maintain the one or more protrusions 150A in engagement with notches 16A of the lower housing 16. Such an arrangement keeps the internal components of the automatic injector 100 in a substantially fixed and locked position capable of being stored and transported for extended periods of time. This configuration of the sleeve 150 also functions to maintain the position of the syringe barrel 202 and needle assembly 40 within the housing during, for example, removal of the needle shield 52. Additionally or alternatively, the sleeve 150 may be used to brace against barrel 202 of syringe cartridge 20 to ensure substantially axial alignment of these components during storage, transport, and operation of the actuation mechanism and automatic injector. Upon removal of the cap 18, protrusions 150A are permitted to flex radially inwards and disengage from the notches 16A. Accordingly, these components function as a safety feature and, upon removal of the cap 18, permit axial translation in the distal direction of the internal components of the automatic injector 100. The cap 18 may also include one or more surfaces 18B to engage needle shield 52 such that removal of the cap 18 by the user prior to activation also removes the needle shield 52 from the needle assembly.

Axial translation of the syringe cartridge 20 may be associated with axial translation of the sleeve 150 during other stages of operation, through the interaction between the release ring 23 of the syringe cartridge 20 and the proximal end of sleeve 150. For example, upon removal of the cap 18 and activation of the automatic injector 100 by the user, the actuation mechanism 30 may cause syringe cartridge 20 to move distally in the axial direction for needle insertion. Through the interaction between the release ring 23 and the sleeve 150, sleeve 150 is also caused to move distally in the axial direction. Sleeve 150 may be translated distally until a bridge portion 150B of sleeve 150 contacts a corresponding depth limiter 16B (visible in FIG. 2) on an interior surface of the lower housing 16. Because of the interaction between release ring 23 and sleeve 150, limiting the range of motion of sleeve 150 also limits axial translation of release ring 23, syringe barrel 21, and syringe cartridge 20 having needle assembly 40. Accordingly, depth of needle insertion into a user can be controlled by the interaction between the bridge portion 150B of sleeve 150 and the depth limiter 16B of lower housing 16. For example, for intramuscular drug delivery (i.e., delivery into the muscle tissue of a user) the insertion depth may be greater and the depth limiter 16B may be located in a more distal position within the interior surface of the lower housing. For subcutaneous drug delivery, the depth limiter 16B may be located in a more proximal position within the interior surface of the lower housing and/or the bridge portion 150B of the sleeve 150 may be located at a more distal position of sleeve 150. FIG. 2 also shows these aspects of sleeve 150, lower housing 16, and cap 18 for additional clarity.

Figure 4:
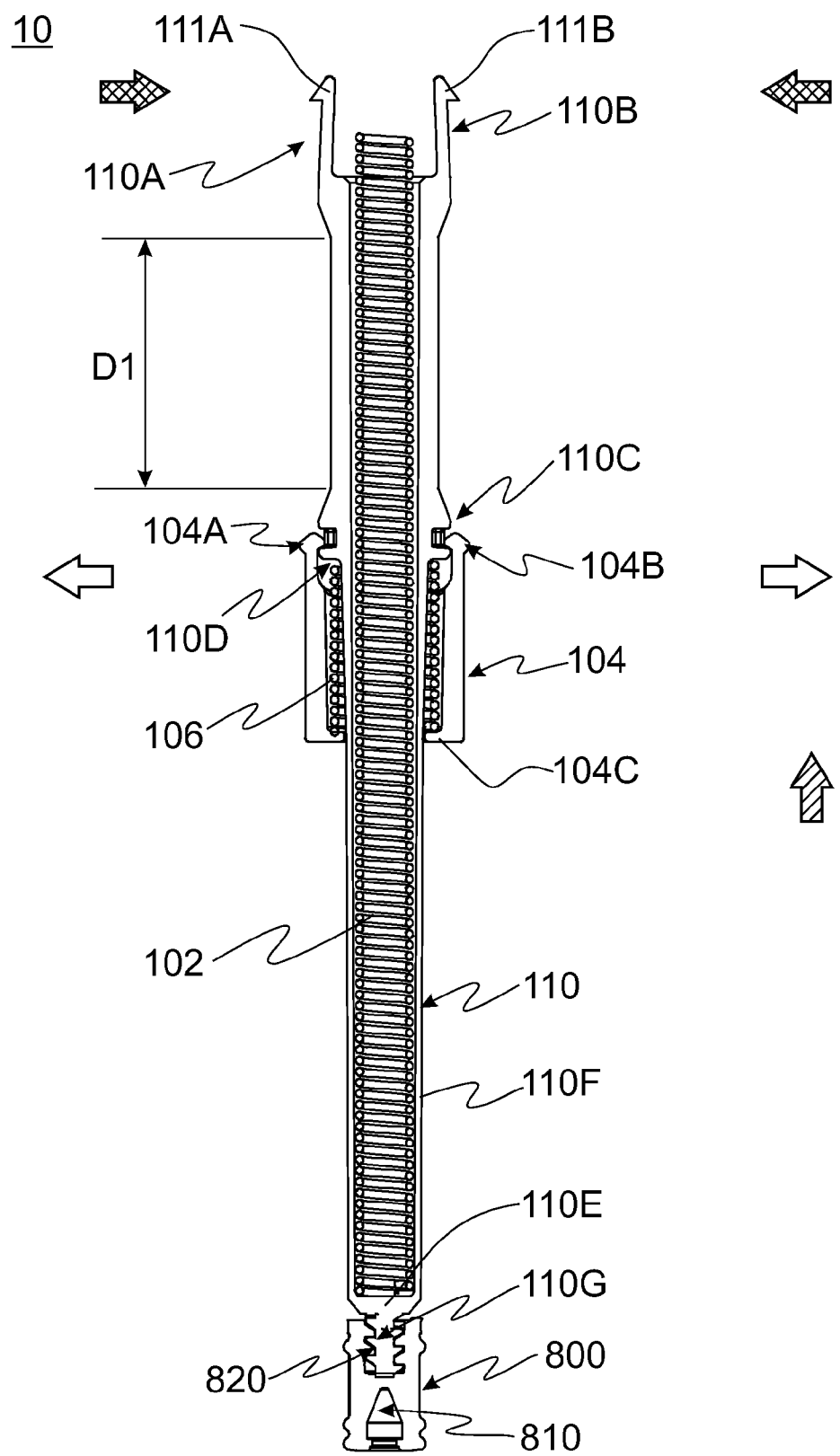
FIG. 4 shows a cross-sectional view of another embodiment of the plunger sub-assembly for an automatic injector, in a configuration capable of retracting a needle assembly upon or after completion of drug delivery.

As described above, the embodiments of the present invention minimize the force necessary to initiate activation of the retraction mechanism. Because the plunger and the integrated retraction features are driven, or caused to activate, by the plunger sub-assembly, the plunger sub-assemblies 10 and the automatic injectors 100 of the present invention may be configured to utilize lower force biasing members, such as compression spring 102, 106. This advantage of the plunger sub-assemblies 10 of the present invention, and their integration into the automatic injectors 100, provides substantial benefits to the manufacturability, stability, and operability of the novel automatic injectors described herein. In at least one embodiment, as shown in FIG. 4, the plunger sub-assembly 10 comprises plunger inner 110 comprising shaft 110F, platform 110E, ledge 110D, engagement slot(s) 110C, locking members 110A,B respectively comprising locking hooks 111A,B and seal-engaging member 110G, which in this embodiment is a screw-threaded projection at the distal end of plunger sub-assembly 10. Seal-engaging member 110E engages complementary, screw-threaded recess 820 of plunger seal 800. Plunger seal 800 further comprises needle-engaging portion 810. Plunger sub-assembly 10 further comprises plunger outer 104 having base 104B and one or more engagement prongs 104A. Plunger sub-assembly 10 further comprises retraction spring 106 which is mounted between plunger inner 110 and plunger outer 104, and held in an initial first energized state between ledge 110D of plunger inner 110 and base 104B of plunger outer 104.

Initially, engagement prongs 104A are caused to releasably engage corresponding engagement slots 110B of plunger inner 110. Engagement prongs 104A,B are held in releasable engagement with respective engagement slots 110A,B by inward radial flexion caused by contact between the engagement prongs 104A,B and a first inner diameter or inner surface of upper housing 14. However, engagement prongs 104A,B of plunger outer 104 are resiliently flexible and flex radially outwards (in the direction of the hollow arrows shown in FIG. 4) when the engagement prongs 104A,B are no longer compressed or flexed radially inwards by the upper housing 14. This can occur, for example, when the plunger sub-assembly 10 is caused to axially translate in the distal direction to a portion of the housing (e.g., the lower housing 16) having a second inner diameter or inner surface that is wider than the first inner diameter. Once the engagement prongs 104A,B disengage engagement slots 110A,B of plunger inner 110, the plunger outer 104 is disengaged from plunger inner 110 to facilitate expansion of retraction spring 106 (in the direction of the hatched arrow shown in FIG. 4) from a first energized state to a second expanded state as part of the integrated retraction mechanism, as will be described hereinafter. Such embodiments of the plunger sub-assembly 10 provide activation of the retraction mechanism without additional force being applied by the actuation mechanism. Accordingly, without additional force being applied by the actuation mechanism on the plunger sub-assembly 10, the retraction mechanism of the plunger sub-assembly 10 is permitted to activate once the engagement prongs 104A,B reach a portion of the lower housing 16 having a second inner diameter or inner surface that is wider than the first inner diameter. Preferably, the second inner diameter is located and dimensioned at a portion of the housing 11 that suitably coincides with the plunger seal 800 pushing out all of the drug fluid through the cannula 411 and activation of the retraction mechanism. In at least one embodiment of the automatic injector 100, the second inner diameter is located in the upper housing 14, the lower housing 16, at the connection between the upper and lower housings 14, 16, and/or at any portion thereof that suitably coincides with the plunger seal 800 pushing out all of the drug fluid through the cannula 411 and activation of the retraction mechanism.

Figure 8:
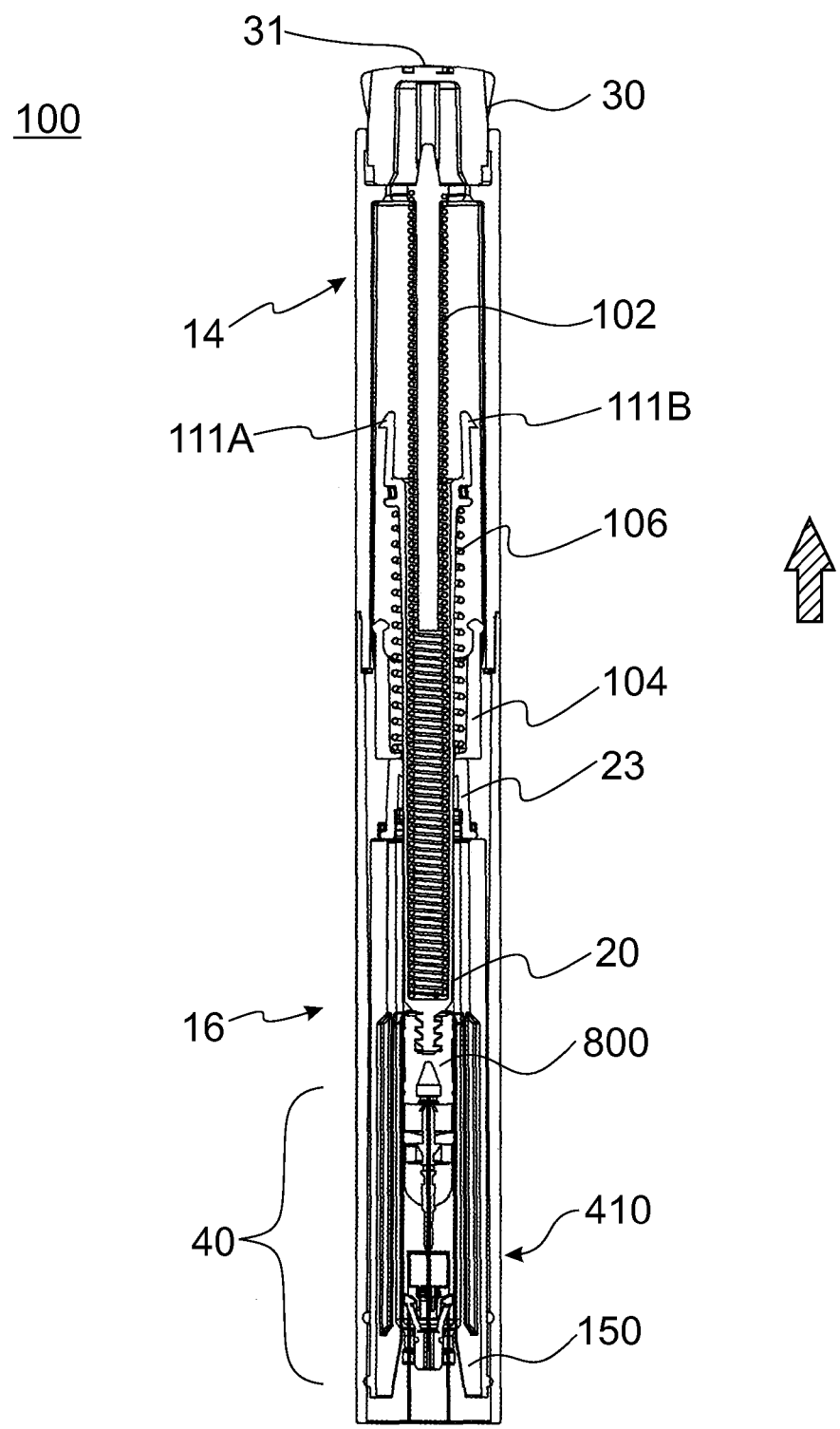
FIG. 8 shows an automatic injector including a plunger sub-assembly, according to one embodiment of the present invention, in a second expanded state and retraction completed configuration.
Figure 9:
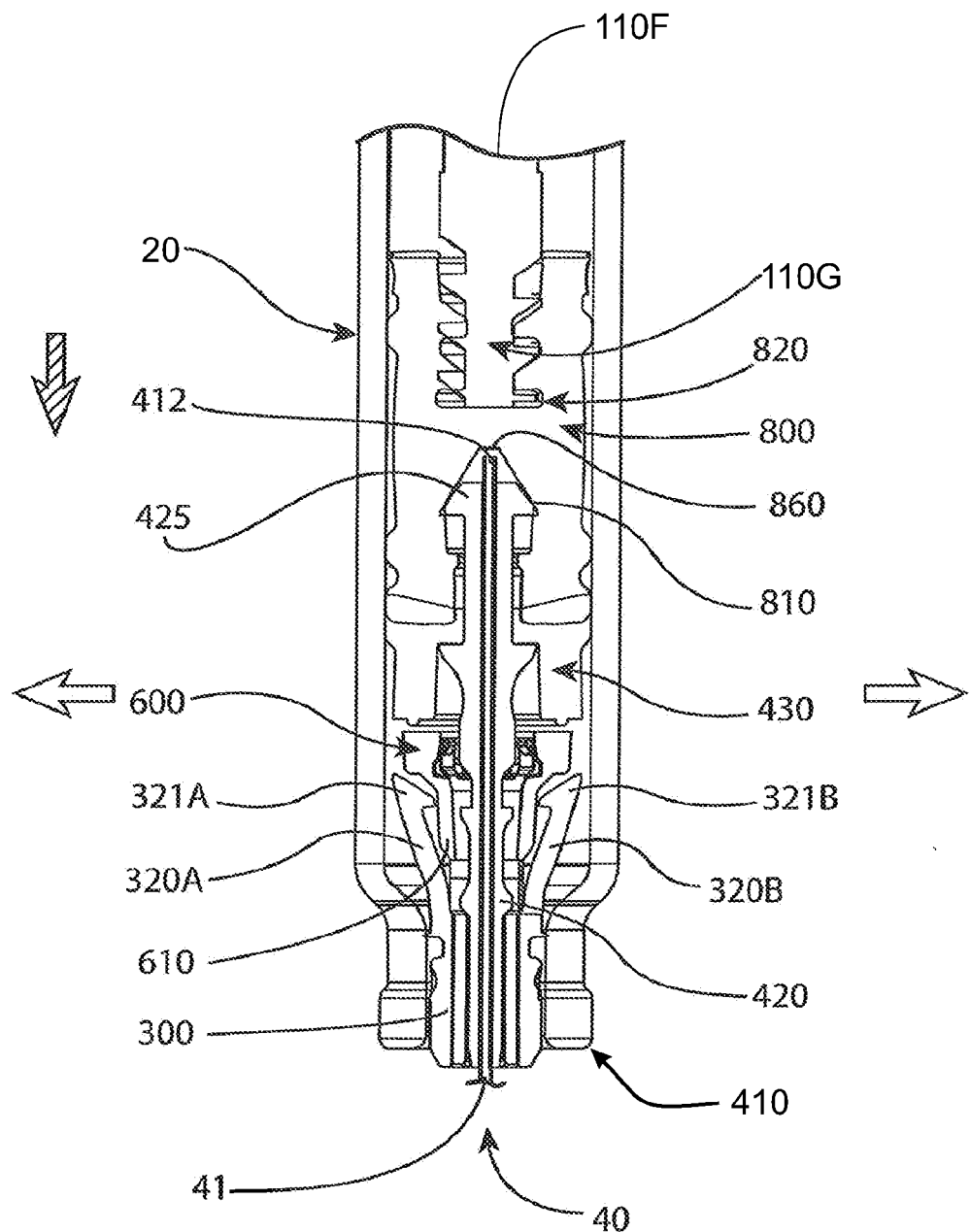
FIG. 9 shows an embodiment of a needle assembly engaged by a plunger prior to retraction.

In at least one embodiment needle assembly 40 integrates a retraction mechanism as described in International PCT App. No. PCT/AU2010/001677, which is incorporated by reference herein. As shown in FIG. 9, such a needle assembly 40 includes retractable needle 410 comprising cannula 411, needle body 420, needle seal 430, retainer 300 and ejector 600. The needle assembly 40 is mounted into the distal end 24 of barrel 21 of the syringe cartridge 20. FIG. 9 shows the components in the retraction activation stage, when contact between plunger seal 800 and needle body 420, needle seal 430 drives ejector 600 to bear against arms 320A, B of retainer 300 to thereby cause hook-ends 321A, B of retainer 300 to disengage from needle body 420 for retraction. Cannula 411 may be a number of fluid tubes but is preferably a rigid needle, such as a rigid steel needle. Prior to or upon retraction activation, plunger recess 860 of plunger seal 800 engages proximal segment 425 of needle body 420 for retraction of needle body 42- and cannula 411. The retraction activation stage is detailed further with reference to the operation of automatic injector 100 in FIGS. 5-8 hereinafter. FIG. 9 shows just one embodiment of the needle assembly 40 configurable for use within an automatic injector 100. A number of other needle assemblies having integrated retraction mechanisms may similarly be utilized. For example, in at least one embodiment the needle assembly may integrate a retraction mechanism as described in International PCT App. Nos. PCT/US2012/067793 or PCT/US2014/024781, both of which are incorporated herein by reference, which do not require a needle body and which activate refraction of the cannula generally through contact between the plunger seal and needle seal.

Operation of plunger sub-assembly 10 and automatic injector 100 will be described with particular reference to FIGS. 1, 2, and 3D, and FIGS. 5-8. In these embodiments, drug chamber 22 of syringe cartridge 20 contains a fluid suitable for injection into a user. As evident in FIG. 5, safety cap 18 (shown also in FIG. 1A) is removable from lower housing 16 to allow activation of the automatic injector 100, insertion of the needle 41 and/or cannula 411 into a recipient, and drug delivery. Initially, activation mechanism 30 is in a locked configuration enabled by the releasable engagement between locking prong(s) 14E (visible in FIG. 3C) of upper housing 14 and locking grooves 32 (visible in FIG. 1B) of activation mechanism 30. Locking grooves 32 may be channels, recesses, detents, or the like along the radial circumference of the activation mechanism, as shown in FIG. 1B, within which one or more locking prong(s) 14E may travel. Initially, the locking prongs 14E are in a position within the locking grooves 30A which prevents depression of the activation mechanism 30. The button 31 of activation mechanism 30 may be rotated around the longitudinal axis to an unlocked position, where the locking prongs 14E are aligned with a portion of the locking grooves 12A that permits axial depression of the button 31. Optionally, an activation spring may be retained within the activation mechanism 30 and/or between the activation mechanism 30 and the proximal end P of the upper housing 14, for example to maintain the activation mechanism 30 in a locked position until user operation and to provide the user tactile resistance upon activation. Additionally or alternatively, the components of the upper housing 14 and the activation mechanism 30 may themselves be utilized to provide the user tactile resistance upon activation, such as by, for example, the interface between an activation surface 33 of button 31 and a corresponding housing surface 14F. This provides useful user feedback to ensure that the proper injection procedures are followed with the device and that removal of the cap is completed prior to needle insertion and drug injection.

In the configurations shown in FIG. 3D and FIG. 5, locking hooks 110A,B of plunger inner 110 initially engage locking plateau 14A of upper housing 14. After removal of the cap 18 and unlocking of the activation mechanism 30, the automatic injector 100 may be placed in contact with the target location of the user and activated for insertion of needle 41 and/or cannula 411, drug delivery, and needle retraction. As described above, removal of the cap 18 may be configured to also remove needle shield 52 from the needle assembly. Similarly, removal of the cap 18 permits one or more protrusions 150A to flex radially inwards and disengage from the notches 16A of lower housing 16. Accordingly, removal of the cap 18 permits axial translation in the distal direction of the internal components of the automatic injector 100. Upon activation of the automatic injector 100 by the activation mechanism 30, locking hooks 111A,B are caused to move radially inwards and disengage from locking plateau 14A. In at least one embodiment, however, the arrangement of the locking hooks 111A,B and the locking plateau 14A may be reversed such that the hooks 111,A, B are caused to move radially outwards to disengage from the locking plateau 14A, as would readily be appreciated by one having ordinary skill in the art. The trigger of activation mechanism 30 is shown as a depression, i.e., distal translation of button 31 in the distance D2 of FIG. 5 (in the direction of the hatched arrow), which causes locking hooks 111A,B to flex inwards and disengage from locking plateau 14A of the upper housing 14. Upon such disengagement, injection spring 102 is permitted to expand from its energized state, thereby axially translating plunger inner 110 and plunger sub-assembly 10 in the distal direction (in the direction of the hatched arrow in FIG. 5). This stage initiates needle 41 and/or cannula 411 insertion and drug delivery to the patient.

Figure 6:
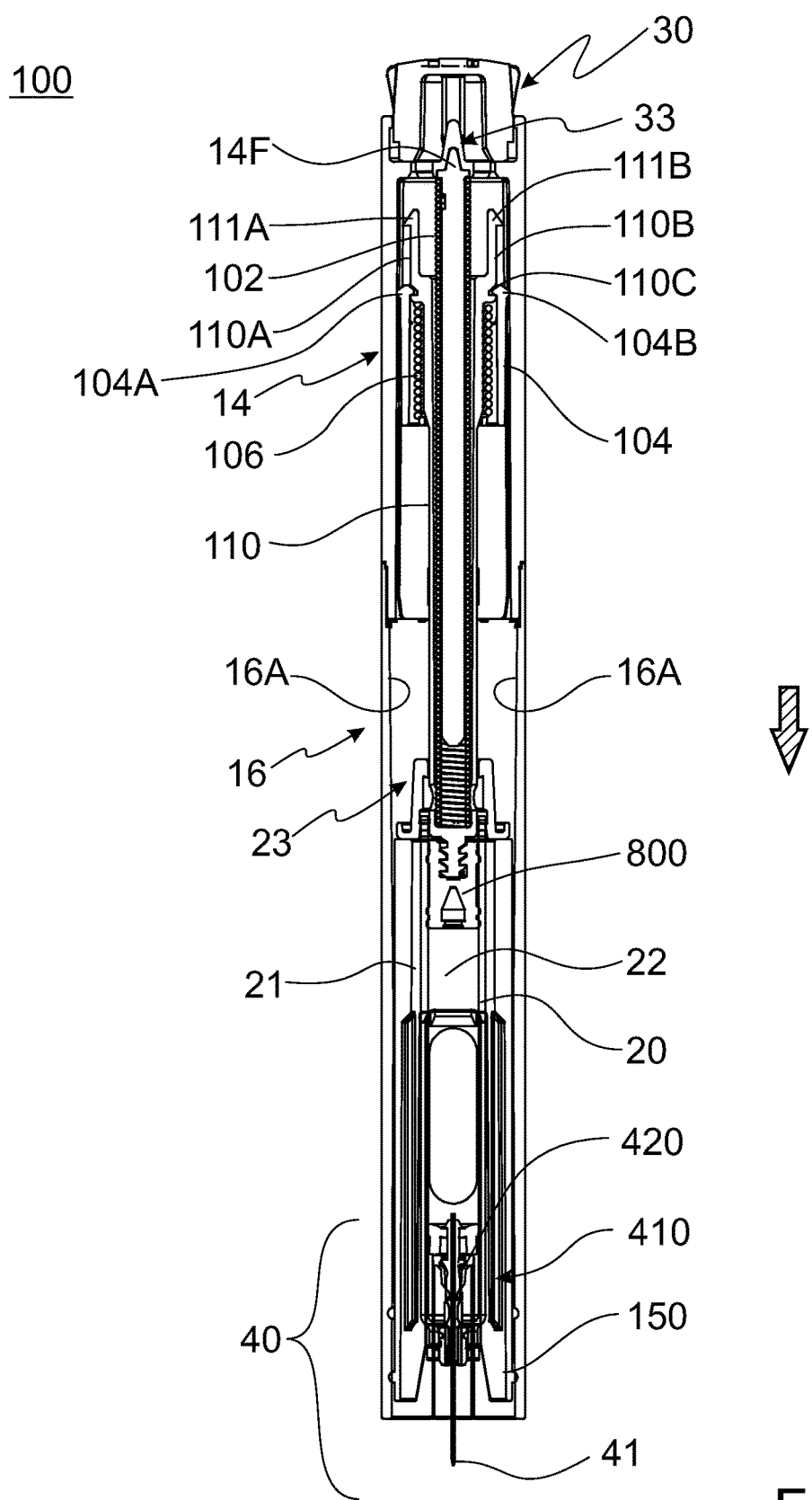
FIG. 6 shows an automatic injector including a plunger sub-assembly, according to one embodiment of the present invention, in an unlocked and activated configuration for needle insertion and drug delivery.

FIGS. 5 and 6 show the automatic injector 100, in a cross-sectional view, before and after activation. Upon activation of the plunger sub-assembly 10, injection spring 102 is permitted to expand from its energized state causing axial translation of the plunger inner 110 and plunger sub-assembly 10 in the distal direction. Distal translation of plunger inner 110 causes distal translation of the plunger outer 104 through the interaction between engagement prongs 104A,B of the plunger outer 104 and the engagement slots 110A,B of the plunger inner 110. At least initially, such distal translation causes the entire syringe cartridge 20 to move with the sleeve 150 in the distal direction for needle insertion (i.e., in the direction of the hatched arrow in FIG. 6), as shown in the transition between FIG. 5 and FIG. 6. As described above, sleeve 150 may be translated distally until a bridge portion 150B of sleeve 150 contacts a corresponding depth limiter 16B on the interior surface of the lower housing 16. Because of the interaction between release ring 23 and sleeve 150, limiting the range of motion of sleeve 150 also limits axial translation of release ring 23, syringe barrel 21, and syringe cartridge 20 having a needle assembly 40. Accordingly, depth of needle 41 and/or cannula 411 insertion into a user can be controlled by the interaction between the bridge portion 150B of sleeve 150 and the depth limiter 16B of lower housing 16.

Figure 7:
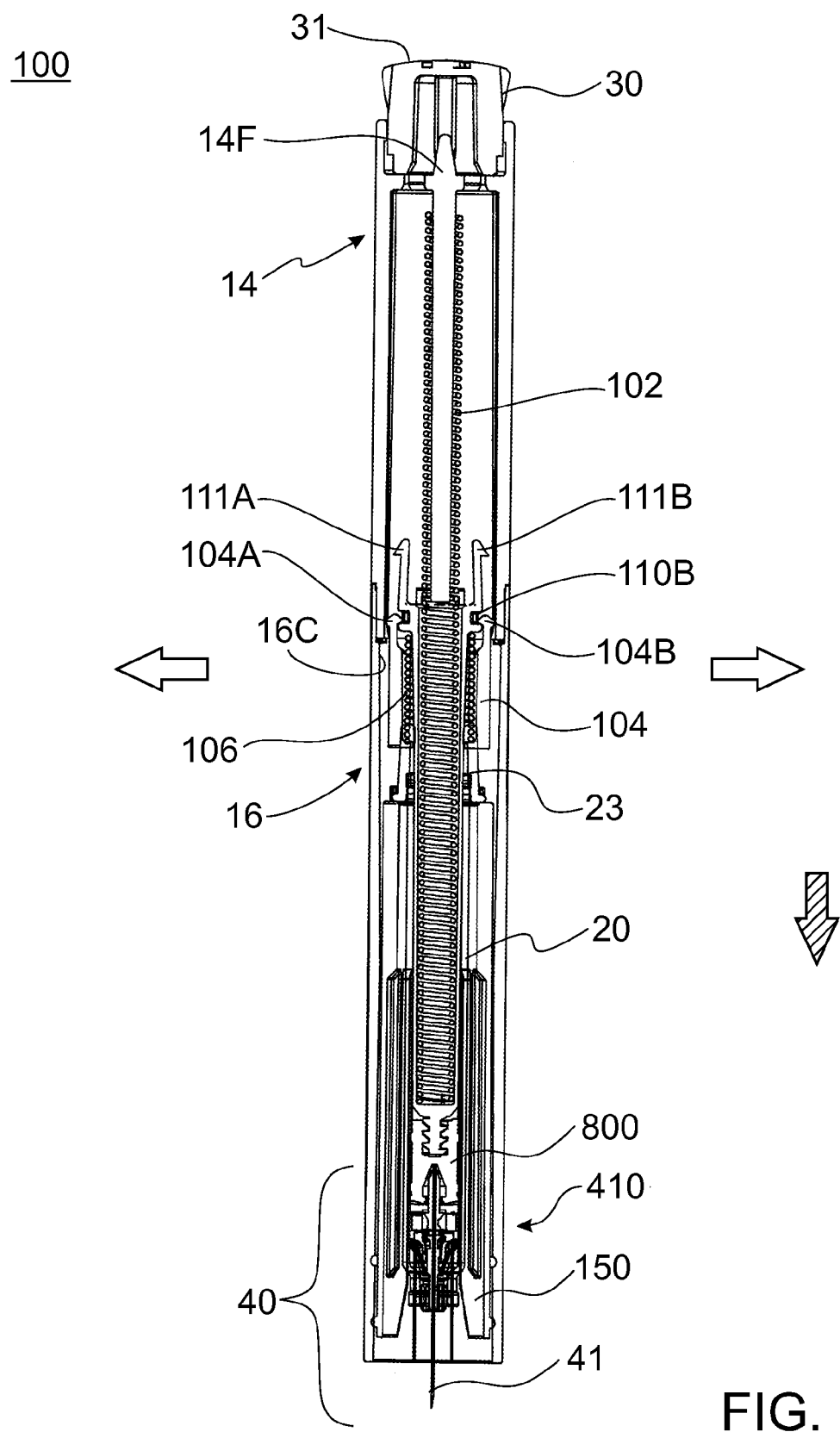
FIG. 7 shows an automatic injector including a plunger sub-assembly, according to one embodiment of the present invention, in a refraction activated configuration.

As the sleeve 150 and syringe cartridge are prevented from further distal translation, the force applied by the injection spring 102 on the plunger inner 110 causes plunger inner 110 to translate distally within the barrel 21 of the syringe cartridge 20. Because the syringe cartridge 20 is prevented from further distal translation, distal translation of the plunger inner 110 within the barrel 21 causes a fluid, such as a liquid drug treatment, to be expelled from drug chamber 22 through cannula 411 of needle assembly 40 and into a user for drug delivery. This is visible in the transition between FIG. 6 and FIG. 7. The dimensions of the components and the lengths of axial travel within the device are configured such that engagement prongs 104A,B of the plunger outer 104 reach the second inner diameter, such as the interior recesses 16C of lower housing 16, substantially at the same time as or after activation of the retraction mechanism within the needle assembly 40. For example, as shown in FIG. 7, in at least one embodiment of the present invention the engagement prongs 104A,B reach the interior recesses 16C of lower housing 16 just after engagement between plunger seal 800 and needle seal 430 of needle assembly 40, effectively ensuring that the recess of needle seal 800 has engagedly captured segment 425 of the needle body 420 of the needle assembly 40 for retraction. The engagement prongs 104A,B are then able to flex radially outwards (i.e., in the direction of the hollow arrows in FIG. 7) and disengage from engagement slots 110A,B of plunger inner 110 for activation of the retraction mechanism. As stated above however, the second inner diameter (e.g., interior recesses 16C) may be located in the upper housing 14, the lower housing 16, at the connection between the upper and lower housings 14, 16, and/or at any portion thereof that suitably coincides with the plunger seal 800 pushing out all of the drug fluid through the needle assembly 40 and activation of the refraction mechanism.

In at least one embodiment of the present invention, needle retraction is essentially similar to that described in International PCT App. No. PCT/AU2010/001677, and will be briefly described as follows with reference to FIGS. 7-11. During delivery of fluid contents, plunger inner 110 moves axially through barrel 21 in the direction of the hatched arrow in FIG. 7. As shown in FIG. 9, plunger seal 800 bears against needle seal 430, which in turn bears against ejector 600. Further to this, ejector ring 610 moves hook-ends 321A, B of arms 320A, B of retainer 300 radially outwardly in the direction of the hollow arrows in FIG. 9, thereby disengaging needle body 420 from retainer 300 to release needle body 420 and cannula 411 for subsequent retraction. At this point, recessed seat 810 of plunger seal 800 has engaged segment 425 of retractable needle body 420 and recess 860 has received fluid end 412 of cannula 411. This effectively couples needle body 420 and cannula 411 to plunger inner 110 since plunger inner 110 is connected to the proximal end of plunger seal 800.

Figure 10:
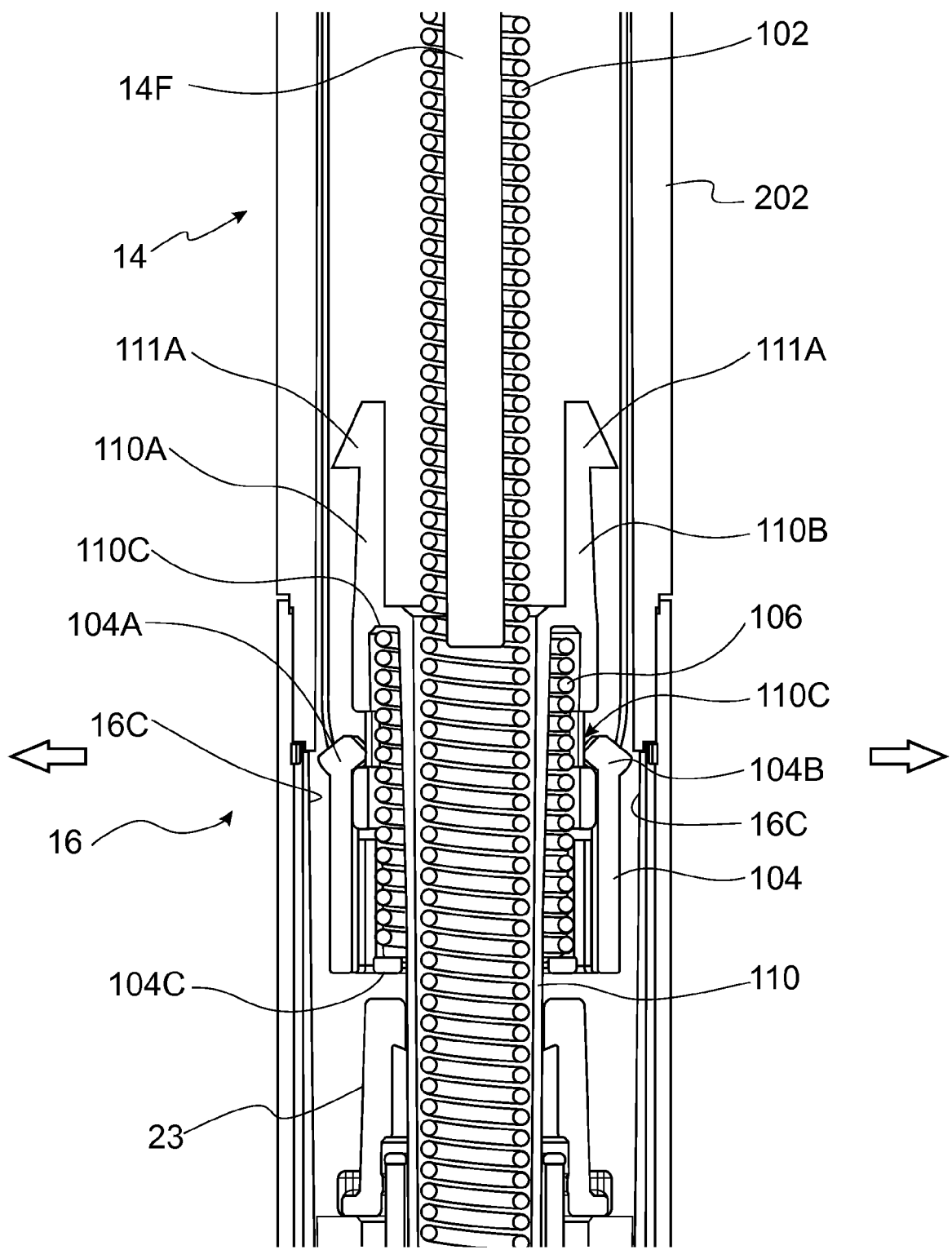
FIG. 10 shows an enlarged view of the retraction activated configuration shown in FIG. 7, in which a plunger outer disengages from a plunger inner to facilitate expansion of the retraction biasing member from its first energized state for needle retraction.
Figure 11:
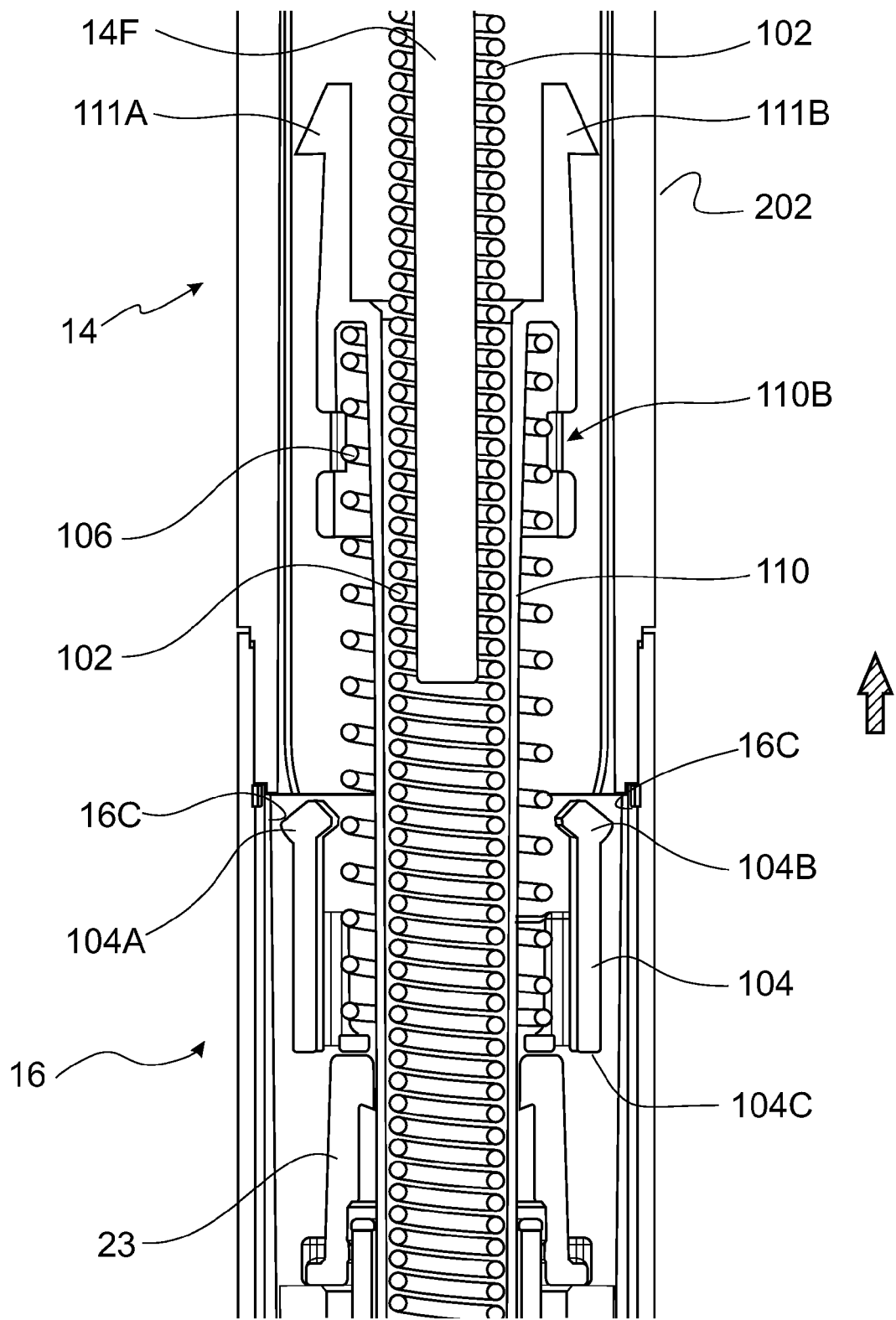
FIG. 11 shows an enlarged view of the second expanded state and retraction completed configuration shown in FIG. 8.

As shown in FIG. 7 and FIG. 10, in order for needle body 420 and cannula 411 to retract at the end of delivery of fluid contents, retraction spring 106 must de-energize to a second expanded state, which is facilitated by plunger outer 104 disengaging from plunger inner 110. This disengagement is without additional force applied by the plunger sub-assembly 10 and, instead, simply by engagement prongs 104A of plunger outer 104 reaching a portion of the housing 11 (e.g., the lower housing 16) having a second inner diameter or inner surface that is wider than the first inner diameter. Accordingly, without additional force being applied by the plunger sub-assembly, the retraction mechanism of the automatic injector 100 is permitted to activate once the engagement prongs 104A,B reach a portion of the housing 11 (e.g., the lower housing 16) having a second inner diameter or inner surface that is wider than the first inner diameter. FIG. 7 and FIG. 10 show this portion of the lower housing 16 having a second inner diameter as recesses 16C of lower housing 16. As plunger inner 110 and plunger outer 104 are substantially fully depressed (i.e., axially translated in the distal direction as per the hatched arrow) to inject fluid from barrel 21, the engagement prongs 104A,B are permitted by the recesses 16C in lower housing 16 to flex radially outwards and disengage from engagement slots 110A,B of plunger inner 110 (i.e., in the direction of the hollow arrows). This disengagement allows a retraction biasing member 106, such as a compression spring, to expand from its energized state and push against ledge 110D (shown in FIG. 4 and FIG. 10) of plunger inner 110 to thereby retract (i.e., translate in the proximal direction) plunger inner 110 with plunger seal 800, needle body 420, and cannula 411 coupled thereto. Plunger outer 104 remains substantially in contact or connection with recesses 16C of lower housing 16, while plunger inner 110 coupled to needle body 420 and cannula 411 is axially translated in the proximal direction by decompression of retraction spring 106, thereby retracting cannula 411 and needle body 420. The simplified design of the plunger sub-assembly 10 and the releasable engagement between engagement prongs 104A, B of plunger outer 104 and engagement slots 110C of plunger inner 110 greatly reduces the force necessary for activation of the retraction mechanism. FIG. 8 and FIG. 11 show the components of the automatic injector 100 with the retraction spring 106 in a second expanded state when needle retraction has completed. At this stage, retractable needle 410 is fully retracted into the housing 11 and/or barrel 20 (i.e., in the direction of the hatched arrow in FIG. 8 and FIG. 11). This needle retraction is highly desirable as it provides integrated safety features while simultaneously providing a true end of dose indication to the user.

Certain optional standard components or variations of automatic injector 100 are contemplated while remaining within the breadth and scope of the present invention. For example, upper or lower housings 14, 16 may optionally contain one or more transparent or translucent windows 50, as shown in FIG. 1, to enable the user to view the operation of the automatic injector 100 or verify that drug dose has completed. Additionally, an optional needle shield 52 may be utilized, as shown in FIG. 5, to protect cannula 411. The needle shield 52 may be connected, for example, to cap 18 and removed prior to operation of the automatic injector 100. Similarly, one or more of the components of automatic injector 100 may be modified while remaining functionally within the breadth and scope of the present invention. For example, as described above, while the housing of automatic injector 100 is shown as two separate components upper housing 14 and lower housing 16, these components may be a single unified component. Similarly, the interior surface of the housing may contain directional channels or guide paths within which the engagement prongs 104A,B may translate to ensure rotational alignment of the internal components during operation. Such standard components and functional variations would be appreciated by one having ordinary skill in the art and are, accordingly, within the breadth and scope of the present invention. It will be appreciated from the foregoing that the plunger sub-assemblies 10 and automatic injectors 100 disclosed herein provide an efficient and easily-operated system for automated drug delivery from a drug container, with integrated safety features and true end of dose indication to the user. Additionally the novel embodiments of the present invention minimize the force requirements for activation of the plunger sub-assemblies, and thereby provide a simplified design for low force safety-integrated automatic injectors.

Assembly and/or manufacturing of plunger sub-assembly 10, automatic injector 100, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization fluids and processes may be employed during the manufacture of the novel components and devices. Furthermore, known sterilization processes may be employed at one or more of the manufacturing or assembly stages to ensure the sterility of the final product.

The automatic injector may be assembled in a number of methodologies. In one method, an injection spring may be inserted into a housing and compressed between the housing and the plunger inner by detachably engaging one or more locking hooks of the plunger inner with a locking plateau of the housing. In this configuration, the injection spring is initially maintained in an energized state substantially within an upper portion of the plunger inner. The plunger outer, with the retraction spring, may then be connected to the plunger inner to form the plunger sub-assembly within the housing. Regardless of the injection spring and plunger inner configuration, a syringe cartridge comprising a plunger sub-assembly, barrel, and needle assembly may be inserted into the housing such that a proximal end of the plunger sub-assembly contacts the upper housing in a locked configuration. Alternatively, the plunger outer may be connected to the plunger inner prior to insertion of the components into the housing. For example, in a preferred embodiment, the plunger sub-assembly containing the plunger inner, the injection spring, the plunger outer, and the retraction spring is first assembled and then inserted and locked into an energized position into the upper housing. This enables, for example, rotational alignment of the plunger sub-assembly, prevents shifting of the plunger sub-assembly from a substantially axial alignment, and helps ensure an even distribution of force onto the plunger sub-assembly upon activation of the actuation mechanism. The syringe cartridge may be a number of syringes such as, for example, a prefilled syringe containing a drug treatment. Preferably, the syringe is a prefilled retractable syringe, as described above. The syringe barrel and needle assembly may be assembled into a lower portion of the housing separate from the upper portion containing the actuation mechanism and plunger sub-assembly. This assembly method may facilitate aseptic filling of the barrel within the housing, insertion of the plunger sub-assembly into the barrel, and connection of the upper and lower housing components for final assembly. The method may further include the step of: attaching an activation mechanism to the housing, wherein the activation mechanism is configured to contact the one or more locking hooks of the actuation pill upon activation. The activation mechanism may be positioned such that it is in a locked configuration for, for example, shipping and storage of the automatic injector. Additionally, the method may include the step of attaching a cap having a needle shield aspect, or attaching separate cap and needle shield, to the distal end of the syringe cartridge and automatic injector.

As discussed above, a glue or adhesive may be utilized to affix one or more components of the automatic injector to each other. Alternatively, one or more components of the automatic injector may be a unified component. For example, the upper housing and lower housing may be separate components affixed together by a glue or adhesive, a screw fit connection, an interference fit, and the like; or the upper housing and lower housing may be a single unified component. These components may be sterilized individually or together, and may be assembled in a sterile environment or sterilized after assembly. Similarly, the assembly of the embodiments of the present invention may utilize a number of other standard manufacturing practices.

The automatic injector may be utilized in a number of different ways. For example, in one embodiment the method of operating an automatic injector includes the step of: (i) disengaging one or more locking hooks of plunger inner or plunger sub-assembly from a locking plateau of a housing, wherein such disengagement permits an injection spring to expand substantially along a longitudinal axis of the housing from its initial energized state. The expansion of the injection spring translates the plunger inner and/or plunger sub-assembly substantially along an axis of the automatic injector in the distal direction. Translation of the plunger inner causes translation of a plunger outer in the distal direction. As one or more engagement prongs of the plunger outer component of the plunger sub-assembly reaches one or more recesses in the inner surface of the housing, the engagement prongs are permitted to disengage from the corresponding engagement slots of the plunger inner. In a preferred embodiment, this disengagement occurs when one or more engagement prongs of the plunger sub-assembly reach a portion of the housing having a wider interior diameter or recess, wherein this occurs just after engagement or contact between plunger seal 800 and needle seal of needle assembly 40. In at least one embodiment, this configuration effectively ensuring that the recess of needle seal 800 has engagedly captured segment 425 of the needle body of the needle assembly 40 for retraction. The plunger sub-assembly may initially drive the needle insertion and drug delivery into the patient. Subsequently, the plunger sub-assembly may activate the retraction mechanism of the syringe cartridge, as described above. The method may further include the steps of: operating the plunger sub-assembly of the automatic injector to deliver a substance to a recipient. Prior to step (i), the method may further include the step of: unlocking an activation mechanism and activating the activation mechanism, as described above.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

The invention claimed is:

1. An automatic injector comprising:
    a housing including an activation mechanism, a proximal end and a distal end, the housing including an inner surface forming an interior, and a locking plateau within the interior, the activation mechanism including a button movable between an initial position and an activated position;
    a syringe cartridge including a barrel, a plunger seal, and a needle assembly mounted to a distal end of the barrel, the needle assembly including a retractable needle, the plunger seal being disposed within the barrel and spaced proximally from the needle assembly, the syringe cartridge being at least partially disposed within the interior of the housing;
    a plunger sub-assembly disposed at least partially within the interior of the housing, the plunger sub-assembly including
        an injection spring,
        a plunger inner having a distal end engaged with the plunger seal, the plunger inner defining a hollow interior with a distally disposed platform, the injection spring being disposed at least partially within the hollow interior of the plunger inner, the plunger inner further including at least one locking hook disposed to releasably engage the locking plateau, engagement of the at least one locking hook with the locking plateau maintaining the injection spring in an energized position at least partially within the hollow interior of the plunger inner between the platform of the plunger inner and the housing, the plunger inner further including at least one engagement slot along an outer surface of the plunger inner,
        a plunger outer disposed at least partially about the outer surface of the plunger inner, the plunger outer having at least one engagement prong disposed to releasably engage the at least one engagement slot of the plunger inner, and
        a retraction biasing member disposed and maintained in an energized state between the plunger inner and the plunger outer when the at least one engagement prong engages the at least one engagement slot,
    wherein movement of the button from the initial position to the activated position disengages the at least one locking hook of the plunger inner from the locking plateau of the housing to permit the injection spring to at least partially deenergize and axially translate the plunger inner and plunger outer in a distal direction within the housing, and
    wherein disengagement of the at least one engagement prong from the at least one engagement slot permits the retraction spring to at least partially deenergize and axially translate the plunger inner in a proximal direction within plunger outer and the housing.

2. The automatic injector of claim 1 wherein the at least one engagement prong is biased radially outward, the at least one engagement prong being held radially inward against the bias and into the engagement with the at least one engagement slot by contact of the at least one engagement prong with the inner surface of the housing.

3. The automatic injector of claim 2 wherein the inner surface of the housing includes at least one recess, alignment of the at least one engagement prong of the plunger outer with the at least one recess permitting substantially outward radial flexion of the engagement prong into the recess to disengage the at least one engagement prong from the at least one engagement slot of the plunger inner to permit release of the retraction biasing member to permit the plunger inner to translate axially in the proximal direction.

4. The automatic injector of claim 3 wherein the plunger outer is held against axial movement in the proximal direction when the at least one engagement prong is disposed adjacent the at least one recess of the housing.

5. The automatic injector of claim 3 wherein the inner surface of the housing includes at least a first inner diameter and a second inner diameter, the second inner diameter of the housing being greater than the first inner diameter, the second inner diameter of the housing being disposed distally of the first inner diameter of the housing, the at least one recess including the housing at the second diameter, the at least one engagement prong held radially inward against the bias and into the engagement with the at least one engagement slot by contact of the at least one engagement prong with the first inner diameter of the housing, and the at least one engagement prong being adapted to disengage from the at least one engagement slot when the plunger outer is disposed with the at least one engagement prong adjacent the second inner diameter of the housing.

6. The automatic injector of claim 5 wherein the housing includes upper housing and a lower housing, the upper housing including the first inner diameter, and the lower housing including the second inner diameter.

7. The automatic injector of claim 6 wherein the upper housing includes a distal surface, the plunger outer being held against axial movement in the proximal direction when the at least one engagement prong is disposed adjacent the second inner diameter of the lower housing and the distal surface of the upper housing.

8. The automatic injector of claim 1 wherein the activation mechanism includes at least one angled surface, the at least one angled surface being moveable to disengage the at least one locking hook from the locking plateau.

9. The automatic injector of claim 8 wherein the at least one locking hook includes the angled surface, depression of the button causing the at least one locking hook to flex and disengage from the locking plateau.

10. The automatic injector of claim 1, wherein the button is rotatable and depressible to thereby directly trigger disengagement of the at least one locking hook from the locking plateau of the housing.

11. The automatic injector of claim 1 wherein the plunger outer has two engagement prongs for releasable engagement with respective engagement slots of the plunger inner.

12. The automatic injector of claim 1, wherein the plunger outer includes a base extending radially inward, the plunger inner includes a ledge extending radially outward, and the retraction biasing member is retained in the energized state between the base of the plunger outer and the ledge of the plunger inner.

13. The automatic injector of claim 1, wherein the plunger seal is adapted to engage the retractable needle, axial translation of the plunger inner in the proximal direction retracting the retractable needle at least partially into the syringe cartridge.

14. The automatic injector of claim 1, wherein the retraction biasing member is a spring.

15. The automatic injector of claim 1, wherein the plunger inner includes a seal-engaging member.

16. The automatic injector of claim 15, wherein the seal-engaging member engages a complementary recess of the plunger seal.

17. The automatic injector of claim 16, wherein the seal-engaging member and the complementary recess of the plunger seal each include complementary screw threads.

* * * * *